(12) United States Patent  
Parel et al.

(10) Patent No.: US 12,290,314 B2
(45) Date of Patent: May 6, 2025

(54) NUMERICAL SYSTEM CONTROL OF OPHTHALMIC VISUALIZATION AND IMAGE SYSTEM

(71) Applicant: UNIVERSITY OF MIAMI, Miami, FL (US)

(72) Inventors: Jean-Marie Parel, Miami, FL (US); Alex Gonzalez, Miami, FL (US); Eric Buckland, Miami, FL (US); Cornelis Jan Rowaan, Miami, FL (US); Florence Cabot, Miami, FL (US)

(73) Assignee: University of Miami, Miami, FL (US)

( * ) Notice: Subject to any disclaimer, the term of this patent is extended or adjusted under 35 U.S.C. 154(b) by 817 days.

(21) Appl. No.: 17/434,975

(22) PCT Filed: Feb. 28, 2020

(86) PCT No.: PCT/US2020/020496
§ 371 (c)(1),
(2) Date: Aug. 30, 2021

(87) PCT Pub. No.: WO2020/180729
PCT Pub. Date: Sep. 10, 2020

(65) Prior Publication Data
US 2022/0142467 A1 May 12, 2022

Related U.S. Application Data

(60) Provisional application No. 62/812,685, filed on Mar. 1, 2019.

(51) Int. Cl.
*A61B 3/00* (2006.01)
*A61B 3/135* (2006.01)
(Continued)

(52) U.S. Cl.
CPC .......... *A61B 3/0025* (2013.01); *A61B 3/0041* (2013.01); *A61B 3/0075* (2013.01);
(Continued)

(58) Field of Classification Search
CPC ... A61B 3/0016; A61B 3/0025; A61B 3/0041; A61B 3/0075; A61B 3/0083;
(Continued)

(56) References Cited

U.S. PATENT DOCUMENTS 6,361,167 B1 3/2002 Su et al.
2003/0085621 A1 5/2003 Potega
(Continued)

FOREIGN PATENT DOCUMENTS

| CN | 202074900 U | 12/2011 |
| EP | 363610 A1 | 4/1990 |
| WO | 2013081619 A1 | 6/2013 |

OTHER PUBLICATIONS

International Search Report and Written Opinion for corresponding PCT/US2020/020496, mailed on May 11, 2020, in 19 pages.

*Primary Examiner* — Jack Dinh
(74) *Attorney, Agent, or Firm* — Meunier Carlin & Curfman LLC

(57) ABSTRACT

A system for ophthalmic imaging comprising an ophthalmic device configured to obtain stereoscopic images of an eye of a patient and to transmit the images in real-time to a display device via a network for viewing by practitioners. The ophthalmic device comprises at least an optic assembly, a processing assembly, a slit assembly, such as a slit lamp, and a positioning assembly. Control devices structured to control the ophthalmic device over the network, such as the world wide web, can be disposed at a plurality of locations, and may be remote from the ophthalmic device while providing (Continued)

real time control of the parameters of the ophthalmic device by the practitioner(s) associated therewith.

6 Claims, 15 Drawing Sheets

(51) Int. Cl.
*A61B 3/14* (2006.01)
*A61B 5/06* (2006.01)
*A61N 5/06* (2006.01)

(52) U.S. Cl.
CPC ............ *A61B 3/0083* (2013.01); *A61B 3/135* (2013.01); *A61B 3/145* (2013.01); *A61N 5/0624* (2013.01); *A61N 2005/0642* (2013.01)

(58) Field of Classification Search
CPC ......... A61B 3/132; A61B 3/135; A61B 3/145; G16H 30/40; G16H 40/67; A61N 5/0624; A61N 2005/0642; G03B 35/08
See application file for complete search history.

(56) References Cited

U.S. PATENT DOCUMENTS

| | | |
|---|---|---|
| 2005/0018134 A1 | 1/2005 | Noda et al. |
| 2005/0024587 A1 | 2/2005 | Somani |
| 2005/0254009 A1 | 11/2005 | Baker et al. |
| 2006/0109649 A1 | 5/2006 | Ducharme et al. |
| 2007/0120979 A1 | 5/2007 | Zhang et al. |
| 2015/0085252 A1 | 3/2015 | Fujimura et al. |

NUMERICAL SYSTEM CONTROL OF OPHTHALMIC VISUALIZATION AND IMAGE SYSTEM

TECHNICAL FIELD

The present invention relates to ophthalmology, and teleophthalmology and telemedicine in a manner that can achieve optimized and clinically operative diagnostic and viewing capabilities by providing a practitioner(s) in a remote location a dynamic high quality and high resolution stereoscopic image of a patient's eye in real time, for example, while interviewing the patient.

BACKGROUND

In ophthalmology, a slit-lamp biomicroscope is generally used as a fundamental diagnostic device to view and assess the anterior and posterior segments of the eye. Typically, examination with a slit-lamp biomicroscope must be performed by a specialist, such as an ophthalmologist or optometrist, in person. That is to say, the specialist performing the examination and the patient must be at the same location since the specialist must be able to view into the eye of the patient with sufficient detail and clarity to perform the diagnosis. This usually means having a three-dimensional view of the eye, as is possible with direct viewing, as more than mere surface analysis of the eye is required in most if not all instances.

Unfortunately, there are many situations in which it is difficult to get an ophthalmic specialist to a patient needing a professional in-depth examination of their eye(s), and/or a second opinion or consultation, in order to conduct the examination, or vice versa. For example, many people in certain countries, such as third world countries, live in rural areas that are difficult and/or time-consuming to reach, especially for a limited number of cases. Moreover, there are some areas of the world in which travel is prohibited and/or dangerous, such as in conflict and combat zones, areas of military action, civil unrest, and other dangerous locations which, nevertheless, have people in need of more than mere cursory eye examination, and in many cases an urgent need due to an eye injury and/or other time-sensitive medical issue. There are still other situations in which performing an eye examination in person could be dangerous, such as in the case of incarcerated prisoners who would require transport to and supervision at an ophthalmologist's office or hospital, or in the case of quarantined patients having contagious or infectious disease(s). There are also situations wherein it may be desirable to use an examination as a teaching or demonstrative opportunity to a plurality of individuals such that it would be impractical to have multiple examinations being performed on the patient, and for multiple eye specialists to view the same eye at the same time for consultation and/or combined examination and diagnosis.

To meet some of the general needs of remote medicine, telemedicine is a growing field utilizing information technology and telecommunications to provide health care from a distance. Although in a limited manner, this type of care has sought to be applied to the ophthalmology field as well. Specifically, teleophthalmology is the use of telecommunications to provide ophthalmological care at a distance. The common approach to teleophthalmology is to capture still or video images of the patient acquired on-site by a technician who is familiar with the functions and purpose of a diagnostic device, such as a slit-lamp. These images are then subsequently sent minutes or days later to a different location to obtain a diagnosis from a practitioner and/or specialist, such as an ophthalmologist. Unfortunately, even a well-trained technician may fail to acquire pertinent images upon examination, may not obtain sufficient views needed for examination, or may acquire images having anomalies and/or artifacts which result in a failed or erroneous diagnosis, and/or which require follow up examination.

While some efforts may have been made to increase the accuracy of teleophthalmology, including possibly providing some rudimentary remote control of basic slit-lamp parameters and telephony, such crude adaptation do not provide true real time control to the diagnosing ophthalmologist of important operational parameters that they would have access to as part of an in-person examination and which can significantly increase their ability to make a complete diagnosis. For this reason, it would be beneficial to provide a system wherein a remote operator is able to alter the angle between the stereo-microscope and the slit-lamp, a crucial function for adequate ophthalmic examination, and/or is able to control most if not all of the slit parameters (height, width, intensity) and the biomicroscope magnification changer, all functions that are necessary for adequate examination of details in the structures of the eyelid, eyelashes, conjunctiva, limbus, cornea, anterior chamber (cell/flare), its angle, the iris and the crystalline lens or artificial intraocular lens if the patient had undergone cataract extraction with intraocular lens (IOL) implantation.

A further deficiency noted with existingly available teleophthalmology, even if some limited remote manipulation of a slit-lamp were available, is the inability to achieve a three-dimensional stereoview of a patient's eye. Specifically, achieving a three-dimensional view is a crucial function for ophthalmologists and optometrists in that such viewing is a necessity to discriminate particle aggregates, abnormal cells, plasma and or hemorrhages and other moieties as well as damaged structures in the depth of the eye's transparent tissues such as the cornea, anterior chamber and the lens. Normally, when a practitioner conducts an eye examination in person, he/she can see the patient's eye in three-dimensions by virtue of simply being present before them and/or adjusting their own eye's focus. Achieving a similar, truly functional three-dimensional or stereoscopic experience from a distance, in real time is still a deficiency in teleophthalmology. Accordingly, it would be beneficial to have a system which provides for the conducting of an eye examination from a distance which achieves functional and manipulable three-dimensional images, and in a sufficiently high resolution to achieve meaningful diagnostic capabilities approaching those of an in-person examination.

It is recognized that 3-D or stereoscopic images are becoming more commonplace in the entertainment industry. To this end, there are a number of ways to produce stereoscopic or three-dimensional images, each of which require two images taken from two slightly different perspectives. For instance, a right image and left image taken from approximately 50-70 millimeters apart is common.

Stereoscopy, or the viewing of images or objects as three-dimensional, can be achieved through side-by-side stereoscopy or shared viewing stereoscopy. The less common and much more rarely used type of viewing is side-by-side stereoscopy wherein the two images are displayed next to each other, and a stereoscopic (three-dimensional) image is seen by simply looking at the space between the images and letting the eyes relax, called free viewing, or with the use of a prismatic viewer which forces the two images to fuse into a single three-dimensional image.

Conversely, the most common type of three-dimensional viewing utilized is shared viewing stereoscopy, which requires the processing and overlay/overlap of the two images coupled with a filtration type viewer. In particular, in shared viewing, each eye sees only one image as a result of a different filter being placed over each eye. For example, in passive shared viewing, the two images are projected through polarizing filters and are superimposed on a screen, and an observer must utilize eyeglasses containing similarly polarizing filters to see the image. Another passive shared viewing technique involves the commonly known anaglyph, an image made from the superimposition of two images of different colors, wherein complementary filters are worn by each eye to see the three-dimensional image. Interference filters may also be used, dividing the images up into two sets of narrow bands of different colors, one set for each eye. Active shared viewing, on the other hand, such as is employed in many commercially available "3-D" televisions, utilizes liquid crystal shutter glass to block and pass light in synchronization with the images on the screen.

Also, much work has been done in the area of head-mounted displays, virtual reality and augmented reality environments. However, to date, only experimental research systems and a few gaming systems have been demonstrated using this technology with real-time capabilities to provide a three-dimensional image. Other techniques have been demonstrated experimentally, either using lenses that are integrated into the display or using multilayered LCD displays, but these systems require the viewer to stand in designated zones to experience a "3-D" effect, otherwise the screen becomes out-of-focus or the image becomes distorted. In addition, using a spinning mirror coupled with a holographic diffuser and a high-speed projector, three-dimensional images that can be viewed from 360° have been demonstrated. Such systems have been made commercially for medical diagnostics for the fields of neurology and cardiology, as found in the Actuality Systems Perspecta Volumetric 3D Display. Furthermore, real-time display and interaction with three-dimensional holographic images has recently been accomplished in the research laboratories of the University of Southern California.

Presently, however, three-dimensional viewing technology has yet to be effectively recognized as operatively applicable in teleophthalmology and/or translated into operative and truly functional system that maximizes the ability of a skilled practitioner to conduct a three-dimensional analysis of a patient's eye. Indeed, it is recognized that in traditional in-person examination of a patent utilizing devices such as a slit-lamp, not all practitioners are able to properly adjust their focus to see a three-dimensional view of the eye, and thus maximize their diagnostic capabilities. Therefore, it would be highly beneficial to provide a system that allows for effective viewing of a patient's eye in a manner that can generate a truly functional three-dimensional image to a practitioner, can actually help to increase the likelihood that a practitioner will be able to see the three-dimensional image, but which will also provide useable high resolution images such that even a practitioner that cannot readily adjust their focus to see a stereoscopic image, whether with or without aid of a viewer, will still be able to examine the eye. Further, there is a significant need for the development of a remotely operated ophthalmic device, such as a slit-lamp biomicroscope that can enable examination in three-dimensional stereoscopy in real time, thus allowing the practitioner to identify contrasts and adjust their view to maximize their ability to identify aspects that are often difficult or impossible to discern from static images.

SUMMARY

The present invention is directed to numerical control of an ophthalmic visualization and imaging device, such as a slit lamp biomicroscope for ophthalmic imaging employing an ophthalmic device controlled over a network and utilizing stereoscopic, or three-dimensional, images. These images can comprise still frame images or multiple frames that create a video. In this manner the system can be used remotely by a practitioner or a plurality of practitioners simultaneously to dynamically control every aspect of an ophthalmic device in real-time over the network, capture three-dimensional images of the patient's eye(s), view those images, and verbally interact with the patient, all in real-time, and thereby conduct an eye exam on at least a portion of an eye, so that they may vary and refine images as they deem optimal to achieve the diagnosis. Accordingly, using the present system, comprehensive eye examinations can be conducted remotely in as much detail and clarity as if the practitioner(s) was present at the same location as the patient, and in a manner that can benefit from the practitioners' skill and expertise. This is a significant advance over existing technology which only allows for the transmission of static images, two-dimensional video images, and/or only allows for the limited remote control of a slit lamp, often leaving a practitioner at the mercy of a remote technician and/or forcing the practitioner to work with what they have rather than with what they need.

More in particular, the system for ophthalmic imaging of the present invention comprises an ophthalmic device structured to obtain at least two images of at least one eye of a patient and to transmit the images to a practitioner(s) who is at a predetermined location. The predetermined location can be in the same room, although preferably is remotely located, such as in another room, building, city or state, or even another country from the patient being examined. Moreover, there may be a plurality of practitioners disposed at different predetermined locations from one another and from the patient. Each of these practitioners can simultaneously view the same patient's eye, verbally interact with the patient as well as each other, and can take control of the ophthalmic device at any point in time during the examination, as described in greater detail hereinafter.

In order to attain optimal images, the system further comprises a control device disposed at each predetermined location and operatively connected in controlling relation to the ophthalmic device. Included as part of the control device is at least one control member. The practitioner(s) uses the control member(s) to control the various components of the ophthalmic device, described in greater detail hereinafter, so as to achieve a desired image. In a preferred embodiment, the control device communicates control messages generated at the direction of an operator, preferably the practitioner, to the ophthalmic device over a network, such as a computer network, in substantially real time.

Further included with the present system, and preferably at the same location and operatively associated with each control device, is at least one display. The display is structured to receive and display the images obtained by the ophthalmic device for viewing by the practitioner(s). Preferably, the image generated by the display is sufficient to allow a stereoscopic or three-dimensional image to be viewed by the practitioner(s). To this end, it is preferred that the practitioner(s) utilize a corresponding viewer through which the display is viewed and which results in the practitioner(s) seeing a three-dimensional image. As with the control messages, the image data is preferably communicated to the display, either directly or indirectly through a processor associated with the display, via a network. In this regard, since the transmission of the images occurs in substantially real-time, limited only by the speed of the network and processors of the system, the practitioner(s) can discern if peculiarities of the image are artifacts, such as air bubbles, or aspects of the patient's eye, such as a cellular flare, inflammation, particle aggregates, abnormal cells, plasma and or hemorrhages and other moieties as well as damaged structures in the depth of the eye's transparent tissues such as the cornea, anterior chamber and the lens.

Looking in further detail to the ophthalmic device, in at least one embodiment, it comprises an optic assembly disposable in viewing relation to the eye of the patient, at least one image capturing member, and a processing assembly disposable in operatively communicating relation to at least the image capturing member. In some embodiments, the ophthalmic device is a slit lamp biomicroscope including a positioning assembly, a slit assembly, an optic assembly, and an associated processing assembly.

The positioning assembly of the ophthalmic device is operative to adjust the position of the ophthalmic device in three-dimensions, as well as to adjust all of the other parameters of the ophthalmic device. To that end, it preferably comprises at least a first positioning member structured and disposed to position the ophthalmic device in a plurality of operative orientations along a first plane (such as along x-y axes) and a second positioning member structured and disposed to position the ophthalmic device in a plurality of operative orientations along a second plane (such as a z axis).

The slit assembly is structured and collectively disposed to adjust at least one dimension of an illuminating slit of the ophthalmic device. For instance, in at least one embodiment, the slit assembly comprises adjustment members to adjust the slit width, height, and angle, as well as the lamp intensity and magnification of the ophthalmic device.

The optic assembly further comprises a magnifying objective associated with the image capturing member such that the image data of the at least one eye of the patient can be captured at an appropriate magnification. The optic assembly, therefore, is disposable in observing and image-obtaining relation to the eye of a patient.

The processing assembly associated with the ophthalmic device is configured and disposable to receive image data from the optic assembly. It includes transmission capabilities operative to transmit image and audio data, receiving capabilities operative to receive control messages from a control device over the network, and relay capabilities operative to relay the control messages and audio data to the various appropriate components of said ophthalmic device.

The present invention is further directed to a system for optimized stereoscopic viewing at various distances by one or more practitioners (In this regard, practitioners may be defined as trained medical personnel, students and/or other individuals who have a reason to view the images of the eye and recognize diagnostic characteristics). In such an embodiment the display is preferably of sufficient size to allow for one or more practitioners to view the display simultaneously at a common location, each using their own or a shared viewer disposable at a predetermined distance from the display. Specifically, although uniform viewing by all able to see the display may be possible, such as in the case of traditional shared viewing stereoscopy, in the preferred embodiment of the present system, and so as to achieve maximum resolution and clarity of the image, as well as to allow for a viewable non-stereoscopic image if needed, side-by-side stereoscopic viewing is implemented. As such, two images are placed side by side on either one large or multiple displays. In such an embodiment, each viewer is preferably configured and operative for optimized stereoscopic viewing of the image(s) on the display at certain distances. As such, the viewer comprises at least one prism having a prism angle, wherein the prism angle corresponds the predetermined distance from the viewer to the display and the size of the images presented so as to attain optimal viewing from that predetermined distance. For instance, a high power prism is provided for viewing larger images or for shorter distances between the viewer and the display.

The system for optimized stereoscopic viewing includes a plurality of operative predetermined distances between the displayed image(s) and the one or more viewers. By way of example, the viewer may be disposable at a first predetermined distance from the display at which stereoscopic viewing of the image(s) is enabled or at a second predetermined distance from the display, for purposes of the example the first predetermined distance being less than the second predetermined distance. Accordingly, a practitioner can utilize one viewer, or a viewer in a first adjustable configuration at a first predetermined distance, such as a close range as in front of a computer or control device where the image presented is small, such as to perform an eye examination of a patient as described above, or in the first few rows of an auditorium or a viewing room. The same viewer can also be used by a person at a second predetermined distance, such as a long range as in an auditorium or at a presentation where the image presented is large, such as in an instructional and training capacity. However, it is preferred that a second viewer and/or an adjustment to the viewer be achieved to provide a different prism angle determined by the viewing conditions.

The invention further is directed to remotely and precisely provide a target delivery of treatments and provide for image guided delivery of treatments. The invention is further directed at recording and repeating a sequence of numerical operations with the ophthalmic device. These numerical control operations can include a repeating sequence that follow a constant course of diagnosis or treatment of a patient, a repeating sequence that follows a consistent course of diagnosis or treatment of a patient, a sequence presented as a teaching device in coordination with a diagnostic or treatment protocol, a calibration to provide for accurate measurements from the acquired digital images, a calibration that is responsive to change in the relative position of the device with respect to a patient and the focus setting parameters of the device, an operation that measures the dimensions of a physiological or pathological feature of the cornea, an operation that uses the measurements to guide precision application of a treatment, an operation that combines the precision measurements with repeated application of a numerical control sequence to reproduce a diagnostic or therapeutic protocol, and a repeated sequence that is coordinated with repeated automated measurements to monitor and record changes in physiology or pathology over time to monitor a course of a disease, healing or treatment.

The invention is further directed to providing an overlay of digital images presented with a current image for comparative analysis from a complementary imaging device, an overlay of digital images presented with a current image for comparative analysis from a previous point in time. In such an embodiment the complementary image is a topographic map of the cornea or is a cross-sectional image from an ultrasound or optical coherence tomography image.

The invention is further directed to combining the calibration of the numerical control with the overlay image at the equivalent scale and processing the stereoscopic image using techniques of photogrammetry to assess the height or curvature of a cornea or lesion on a cornea.

The use of the side-by-side images viewed through prism viewers has a further advantage of being suitable for use with common display monitors, obviating the need for specific "3D" displays.

The benefits of the present invention are clear. With the present invention, a practitioner or a plurality of practitioners can conduct an eye examination from any location simultaneously and in real-time. Thus, the present system may be used when it is impractical and/or unrealistic to get an ophthalmologist to a patient, or vice versa, such as: in emergency situations where travel time is prohibitive; when the patient is in a remote location such as a rural locale and/or places of restricted access such as military and combat zones; when the patient is quarantined for health or safety reasons, such as contagious infected individuals or prison inmates. The present system is also useful for joint consultations, such as when multiple opinions are desired, as well as for presentation to a large number of people at once, such as in instruction and training during a seminar or class.

These and other objects, features and advantages of the present invention will become clearer when the drawings as well as the detailed description are taken into consideration.

BRIEF DESCRIPTION OF THE FIGURES

For a fuller understanding of the nature of the present invention, reference should be had to the following detailed description taken in connection with the accompanying drawings in which.

DETAILED DESCRIPTION

Figure 1:
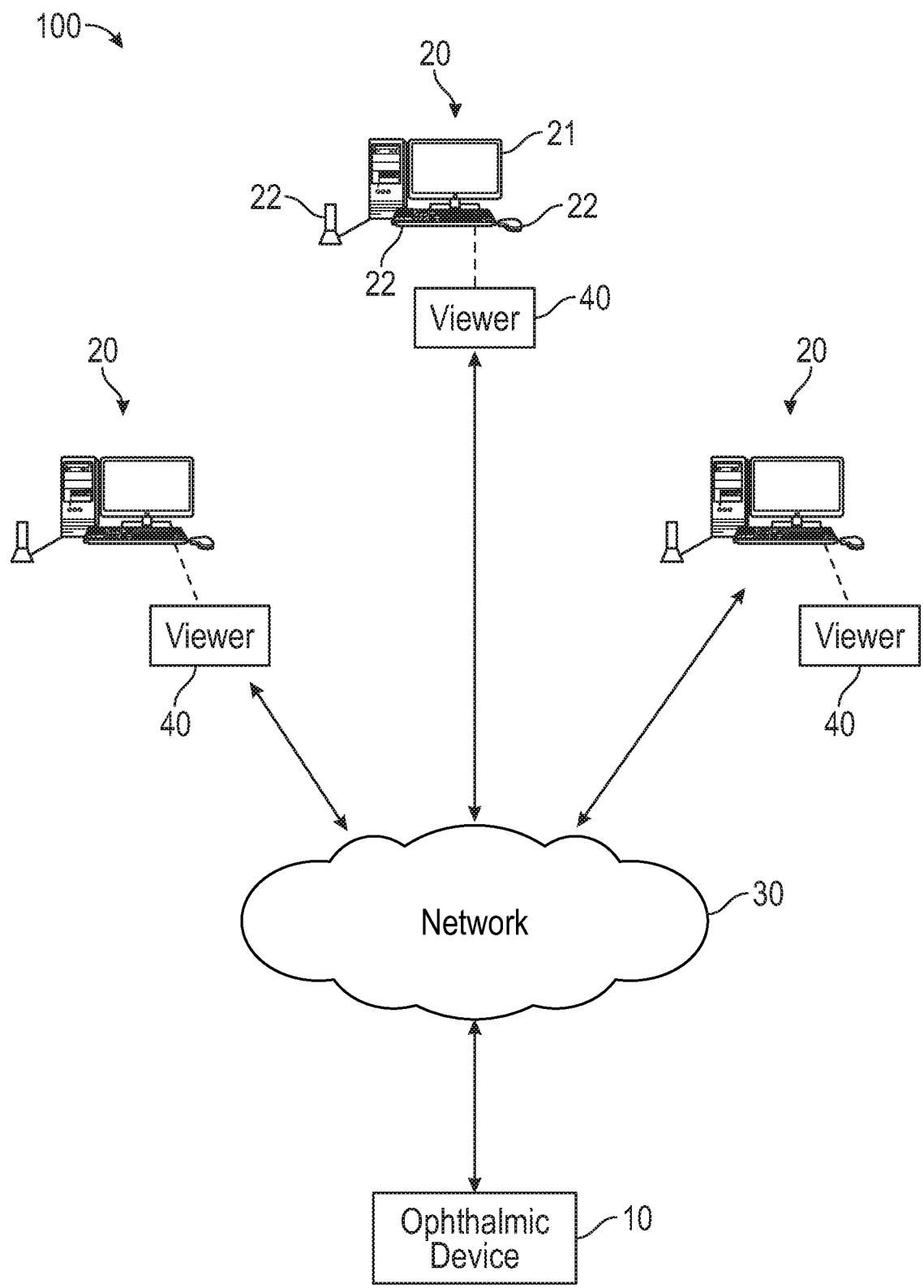
FIG. 1 is a schematic representation of the system for ophthalmic imaging of the present invention.

The present invention is directed to a system for ophthalmic imaging employing an ophthalmic device controlled over a network and utilizing stereoscopic, or three-dimensional, images. As shown in FIG. 1, the system for ophthalmic imaging 100 comprises an ophthalmic device 10 structured to obtain stereoscopic images of at least one eye of a patient and to transmit these stereoscopic images to at least one practitioner at a predetermined location(s) so that the practitioner(s) may view a true three-dimensional image of the eye. The system 100 further comprises a control device 20. The control device 20 is preferably also disposed at the predetermined location(s) and is connected in communicative relation with the ophthalmic device 10 over a network 30, such as a computer network and/or the Internet, so as to provide for effective control and manipulation of the ophthalmic device 10 as needed and directed by the practitioner(s).

As depicted schematically in FIG. 1, the system 100 comprises at least one, but preferably a plurality of predetermined locations of the control device(s) 20 defined as the location where the practitioner(s), who will preferably be operating the control device 20, are present, and as such, are preferably locations that are separate and distinct from the location of the ophthalmic device 10, as well as from other practitioners. For example, one practitioner or a plurality of practitioners at disparate locations can simultaneously view and interact with the patient, as well as converse with each other. Moreover, since each practitioner is associated with a control device 20, any of the practitioners involved in remote examination utilizing the present invention may take control of and direct the movements of the ophthalmic device 10 at any time during the examination through the use of their respective control device 20, as described in greater detail hereinafter. Therefore, in preferred embodiments the practitioner(s) will be in a position to directly operate the control device 20, and as such both the practitioner(s) and the control device(s) 20 will be at a remote location(s), whether a few feet away from the ophthalmic device 10, in a different room or building from the ophthalmic device 10, or an entirely different state, country or continent. Of course, the predetermined location may be the same location as that of the ophthalmic device 10 such that an operator controls the control device 20 at the direction of a practitioner.

Regardless of the embodiment, each control device 20 is disposed in controlling relation to the ophthalmic device 10, such that a practitioner(s), using the control device 20, can direct changes in the positioning and parameters of the various components of the ophthalmic device 10, as will be described in greater detail subsequently, thereby achieving the optimal views and images of the eye that they require. In at least one embodiment, such as shown in FIG. 1, the control device 20 includes a computer processor such as a desktop computer, a laptop, portable or mobile device such as a tablet or smartphone, or any other processor capable of receiving control inputs and audio data and communicating those in the form of control messages via a network to the ophthalmic device 10.

Operatively associated with the control device 20, and preferably at the same location as the control device 20 is at least one display 21 configured to present image data received from the ophthalmic device 10. The display is sized appropriately to the viewing environment desired by the practitioner(s). For example, in the embodiment of FIG. 1, the display 21 comprises a video monitor while in other embodiments, the display 21 comprises a screen that can receive a projected image thereupon, such as in an auditorium, classroom, or other appropriately sized screen for displaying the image to multiple people at once, as depicted schematically in FIG. 12. Moreover, in other embodiments, the display 21 is smaller, such as the screen of a laptop computer, tablet, smartphone, or other portable computing device. Nevertheless, as will be described in greater detail subsequently, in order to achieve optimum resolution and thereby attain a truly diagnostically beneficial stereoscopic image, a very high resolution display large enough to accommodate a pair of large side by side images and/or a pair of high resolution displays, is preferred.

The control device 20 further comprises at least one control member 22 having directing capabilities operative to control movement of the ophthalmic device 10 and its various components. Accordingly, the control device 20 also comprises software and/or firmware to interpret the movements and inputs of the control member 22 and convert such movements into control messages to be sent over the network 30 to direct movement of the ophthalmic device 10, as needed by the practitioner(s). For example, individual or collective multi-step control messages are directed to the various different components of the ophthalmic device 10, such as to move the entire device in a particular manner, or to move one component in a particular manner, as described in further detail below.

In some embodiments, such as the one shown in FIG. 1, the control member 22 comprises a keyboard, wherein different keys on the keyboard initiate different control messages to perform different functions. In other preferred embodiments, the control member 22 may comprise, instead of or in addition to a keyboard, a joystick type control which is used to direct movement of the ophthalmic device 10 by moving the joystick in certain directions, and which may also include a number of buttons or inputs which may be selected to achieve certain functions and/or mark locations for comparative, recall or other purposes. In still other embodiments, the control member 22 may comprise a mouse instead of or in addition to a keyboard and/or joystick, wherein movement of the mouse in particular directions and clicking of mouse buttons directs movement to adjust the ophthalmic device 10. Furthermore, the control member 22 may comprise touch screen devices such as a touch sensitive monitor, cellphone, or tablet. For example, the display 21 may be touch sensitive and have digital sliders and knobs that act as the control member 22 to adjust the ophthalmic device 10. It should be appreciated that different control members 22 can be used in the same embodiment, separately or in conjunction, and any of a variety of available or to be developed inputs, including touch screen devices, voice command input devices, simulators or other input devices, could also be used independently and/or in conjunction with one another.

Further in the case of multiple control members 22, each can be assigned different functions and/or some degree of overlap can be provided with either the practitioner and/or a set command priority dictating the control message and the resultant adjustment of the ophthalmic device 10. For example, multiple touch screen devices such as mobile phones can be used collectively or independently to control the ophthalmic device 10. Regardless of the embodiment, the control member(s) 22 is operable by a practitioner located at the control device 20 to direct movement of the ophthalmic device 10 regardless of the location of the ophthalmic device 10 relative thereto.

Looking in further detail to the network 30, as described previously, the control device 20 preferable utilizes a network to communicate the control messages to the ophthalmic device 10, and to receive images generated by the ophthalmic device 10. As will be described, in a preferred embodiment the network 30 utilized by the present system is a computer network, and as such may be a private or public network. By way of example only, the network 30 may comprise an intranet, local area network (LAN), wide area network (WAN), Internet, Wi-Fi, Bluetooth, or other connection between devices structured for the transmission of data. Furthermore, connections to the network 30 can be hardwired, such as through USB, Ethernet, or other connections achieved by physical tangible structure, or may be wireless, such as through wireless Internet connection, Wi-Fi, Bluetooth, satellite, etc.

The data contemplated to be transmitted over the network 30 in the present system 100 comprises information from the ophthalmic device 10 and information from the control device 20. Data from the ophthalmic device 10 includes at least image data of at least one of the patient's eyes, although additional image data such as positional image data of the patient, audio of the patient such as his/her responses to questions and directions from a practitioner(s), interface information such as may be generated by software utilized in the system 100 for the capture and presentation of patient information, and even patient biographic, demographic, and background material, such as patient identifying information and may be found and/or stored in a patient's individual file or chart. Data from the control device 20 includes control messages such as discussed above, audio of the practitioner(s) directed to the patient or other practitioners, and other commands. Accordingly, the network 30 is operative to facilitate transmittal of data, such as image and audio data and control messages between the ophthalmic device 10 and the control device 20.

The image data communicated by the ophthalmic device 10 comprises at least one, but preferably two images of the same eye of a patient captured substantially simultaneously by the ophthalmic device 10 for transmission to and displayed on the at least one display 21 associated with the control device 20 such that a practitioner located at the control device 20 can see a three-dimensional stereoscopic image of the patient's eye. In this regard, however, it is recognized that in the case of an operator other than practitioner controlling the control device, one display may be provided at the control device and another for viewing by the practitioner. Further, a secondary display(s) can be included such as when multiple people or practitioners are viewing the images but only one practitioner is controlling the ophthalmic device 10, such as in a lecture or instructional setting. In any case, the image data can further comprise additional images of the patient, such as providing positional information of the patient in relation to the ophthalmic device 10 and/or positional information regarding the ophthalmic device.

Figure 9:
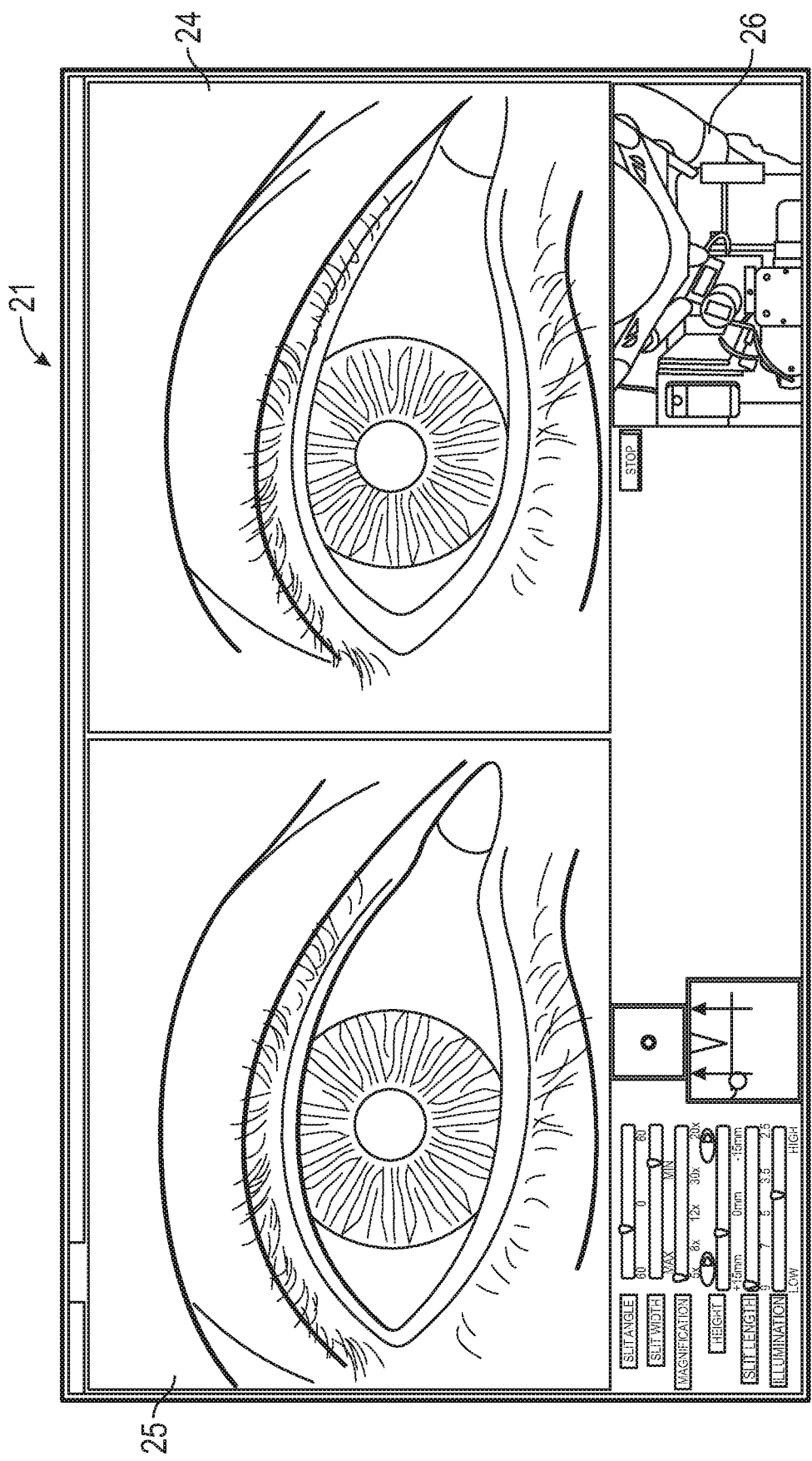
FIG. 9 is a diagram of one embodiment of the display of the present system.
Figure 10:
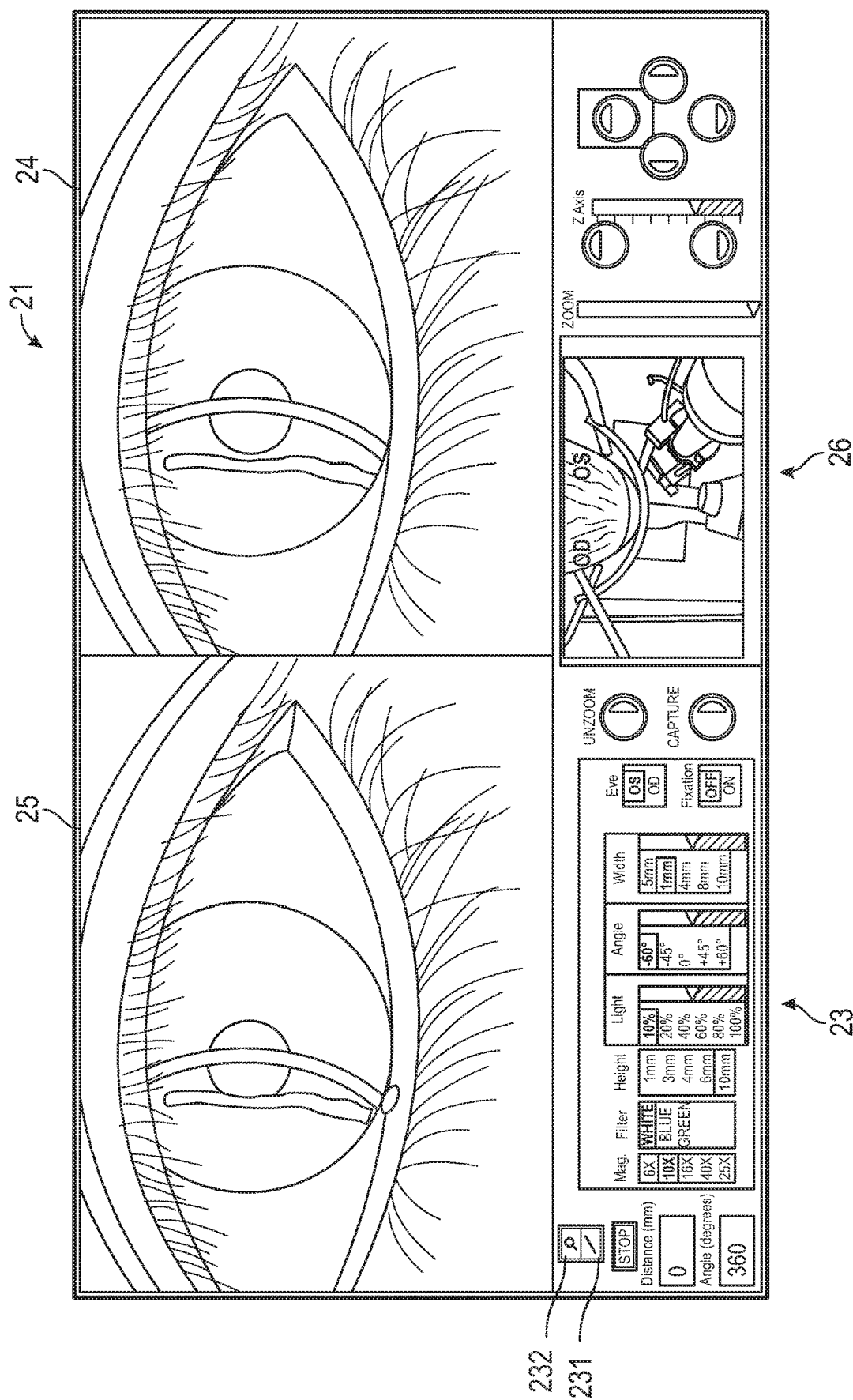
FIG. 10 is a diagram of another embodiment of the display of the present system.

As noted, in a preferred embodiment, two images of the same eye of the patient, taken from slightly different angles, are presented in adjacent non-overlapping relation to one another on one large high resolution display 21, as shown in FIGS. 9 and 10, and/or on a pair of side by side displays, allowing for the preferred fusion three-dimensional viewing of the patient's eye to be achieved, as will be described. Accordingly, the preferred embodiment of the present system 100 comprises side-by-side binocular fusion stereoscopy so as to achieve the maximum possible resolution and clarity of the image, and also to produce images that even if not viewed utilizing a corresponding viewer for stereoscopic diagnosis are still clear and viewable. Alternately, however, it is recognized that other types of stereoscopic images, including offset polarized images, multi-color images and/or other types of 3-D imaging as may be developed, may also be utilized and communicated to correspondingly configured displays capable of displaying such images for three-dimensional viewing utilizing corresponding integral, separate or wearable viewers. As noted, however, despite the availability of 3-D televisions and displays, such overlapping image types of stereoscopic viewing must split resolution over the two images and are often difficult to view and/or are distorted if not viewed using a specific viewer from a specific angle. As such, a binocular fusion type of stereoscopic image is presently preferred in the present invention.

In at least one embodiment, the image data from the ophthalmic device 10 includes high-definition resolution video. As used herein, "high-definition" means higher than standard or traditional definition. For instance, high-definition may be 720p, which is a resolution of 1,280×720 pixels. In an embodiment, high-definition may also be 1080p, which is a resolution of 1,920×1,080 pixels and/or improved levels of definition as may be available and/or developed. In another embodiment high definition may be 4K or 8K, which are resolutions of 3840×2160 pixels and 7680×4320 pixels respectively. The high resolution allows the practitioner to discern the presence of cells and/or flare in the anterior chamber of the eye of a patient. In an embodiment the control device 20 controls the ophthalmic device 10 such that the ophthalmic device 10 locates a patient's pupil, enhances the video for optimal contrast with a dark fundus background, and adjusts the slot width, slit angle, and light intensity, to the optimal settings. The control device 20 can be operable to detect and highlight the region containing cells or flare based on preset visual parameters. It is contemplated that the image data of the patient's eye, and in particular each of the two preferred images have high-definition resolution. Conversely, image data of patient positional information may or may not be high-definition resolution. Further, in at least one embodiment the image data may be compressed and/or encoded into a single multiplexed signal comprising video, audio, and other data, such as with a hardware video encoder or a software encoder, in order to lower bandwidth requirements for transmission. The video compression can be executed via software, with one stream multiplexing, stereo imaging of the eye, patient's overview of the video, and user controls. The data is then transmitted over the network 30, such as at a rate of 15 frames per second and/or other acceptable rates of transmission that the network can accommodate. Furthermore, the ophthalmic device 10 can be operable to detect and sense the resolution of the display 21 of the control device 20 or multiple control devices 20, and the ophthalmic device 10 may be operable to compress or scale down the image data from the original captured resolution to match the resolution of the display 21 of the receiving control device 20. For example, the resolution of a cell phone screen could be smaller than the camera resolution and would benefit from compressed imaged data that results in less data needed to be transmitted and received.

The ophthalmic device 10 is preferably configured to generate and transmit the image data over the available network 30 in substantially real-time relative to data generation, thus providing the practitioner(s) with the closest approximation to in-person viewing of the patient's eye. For example, as soon as images of the patient's eye are captured by the ophthalmic device 10, they are relayed to the display 21 for viewing by the practitioner(s). Similarly, as soon as control messages are generated by a control member 22, they are sent to the ophthalmic device 10 which reacts to the control messages upon receipt. As used herein, "substantially real-time" means as close to instantaneously as possible and is limited only by the limitations of the network and the speed of the processors in the ophthalmic device 10 and control device 20. For example, transmission may be slightly delayed due to the distance covered or the bandwidth available on the network 30. Similarly, transmission may be slightly increased with faster processors used in the ophthalmic device 10 and/or control device 20. However, it should be appreciated that "substantially real-time" means as near in time to the generation of the data as feasible. Accordingly, the network 30 facilitates real-time transmission of data and information, such that at least a portion of an eye examination can be conducted remotely as if the practitioner(s) were in the same room as the patient.

Figure 2A:
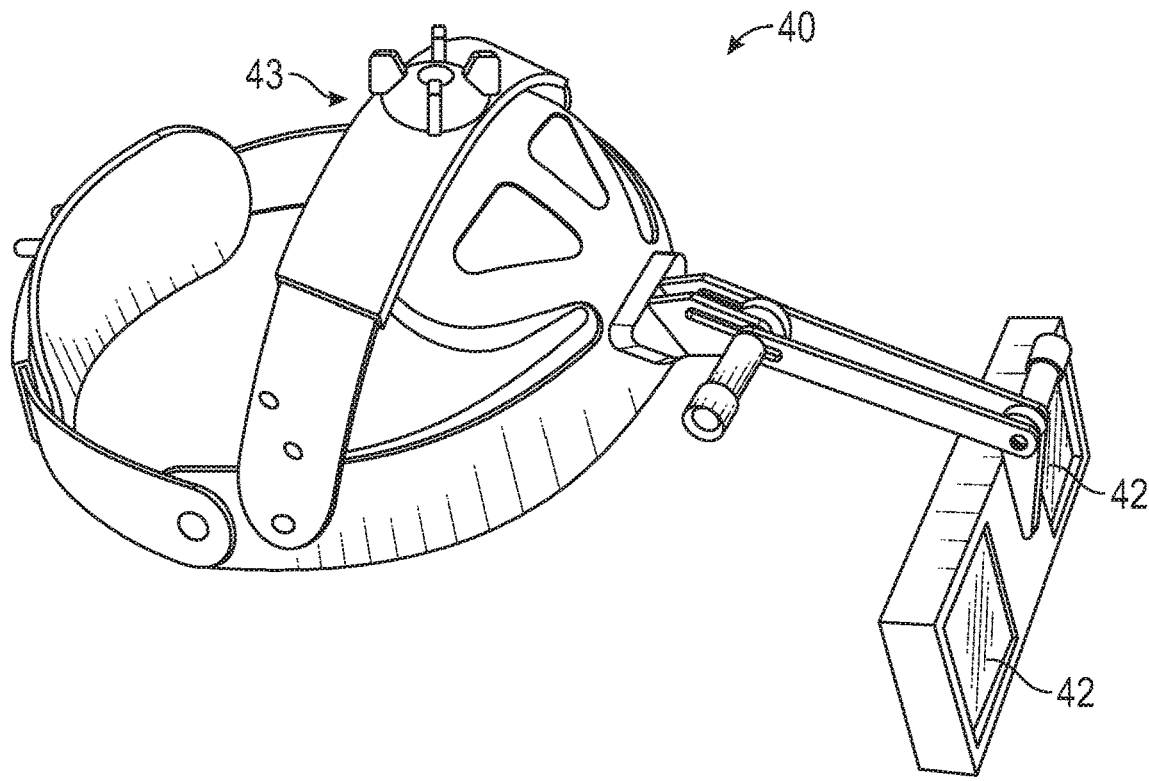
FIG. 2A is a perspective view of one embodiment of the viewer of the present system.
Figure 2B:
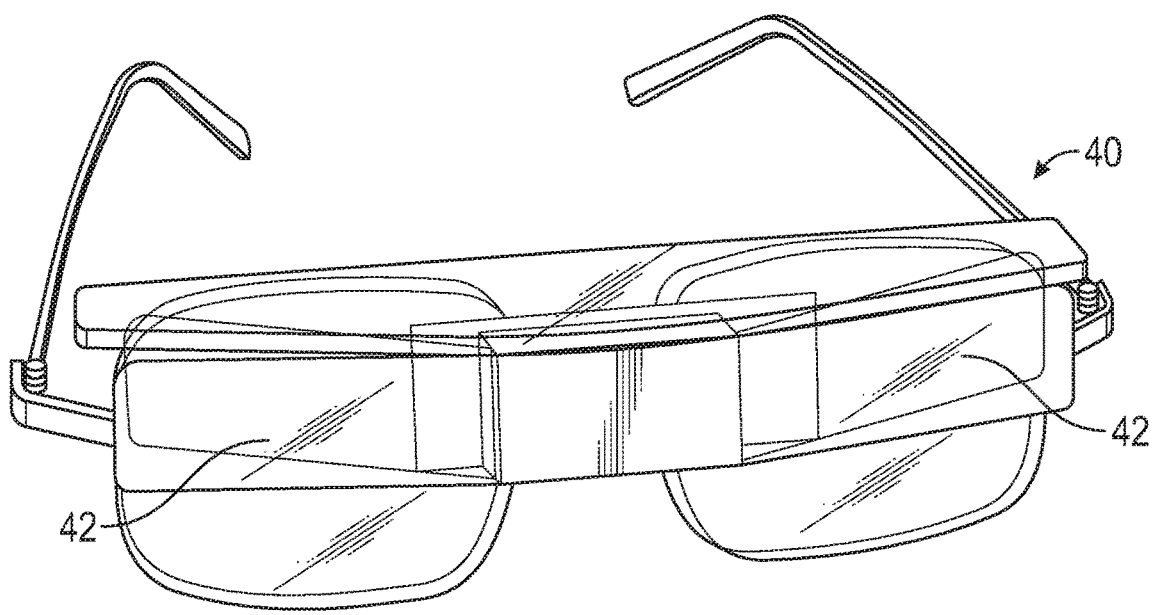
FIG. 2B is a perspective view of another embodiment of the viewer of the present system.

In at least one embodiment of the present invention, as shown in FIGS. 1 and 2A-2B, the system 100 further comprises a viewer 40 structured for stereoscopic viewing of the one or more images displayed on the display(s) 21. Indeed, in many embodiments the viewer 40 is mountable relative to the practitioner, wearable by the practitioner, and/or otherwise capable of being at least temporarily associated with the practitioner to enable viewing there through. Accordingly, in at least one embodiment, as in FIG. 2A, the viewer 40 is mountable to the head of a wearer through the use of a mounting assembly 43. In another embodiment, as in FIG. 2B, the viewer 40 comprises glasses that may be worn on a practitioner's head. Of course, in other embodiments, the viewer 40 can be hand-held by a practitioner during use.

Figure 11:
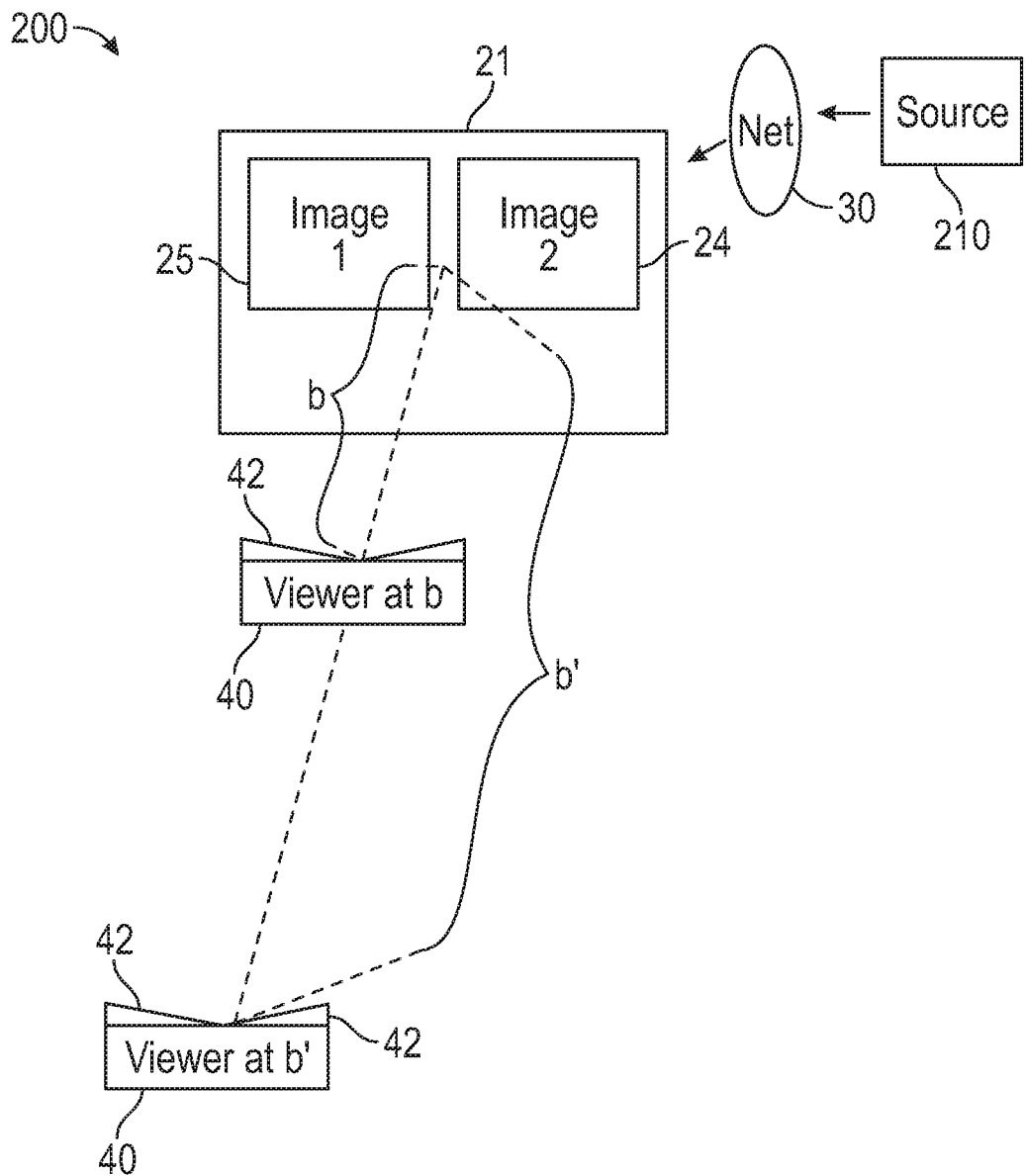
FIG. 11 is a schematic representation of a system for optimized stereoscopic viewing of the present invention.

Although different types of three-dimensional viewers may be used, in at least one embodiment, such as illustrated in FIGS. 2A, 2B, and 11, the viewer 40 comprises at least one prism 42 to enable the combination of two images into a fusion three-dimensional image. Specifically, the preferred pair of prisms 42 are configured to direct one of the two images to each eye in a manner wherein each eye generally views only a single image and wherein the prisms 42 direct the images onto the eye in a manner that causes the two images to appear in the generally same place and thereby provide the stereoscopic appearance required by the practitioner(s) to effectively view the depths of the patient's eye and properly diagnose certain conditions. The prism 42 may comprise any one of a multitude of different prism angles, as will be described in greater detail subsequently, and different viewers 40 may comprise different prisms 42 with different prism angles for various viewing requirements, such as dependent upon the size of the display 21 and/or the distance from the viewer 40 to the display 21. In a preferred embodiment, the viewer 40 comprises two prisms 42, one prism 42 on each lens. In such embodiment, the prisms 42, which should each substantially cover one eye of the examiner or practitioner, are spaced apart, having an interpupillary distance varying from generally about 5.2 centimeters to 7.9 centimeters, with 5.4 centimeters being one example of optimal spacing. It should be appreciated that the above range and distances are approximations only and are not meant to be strictly construed. Indeed, slight variances in the distances are contemplated and are within the scope of the present invention. Alternately, the viewer 40 may merely include an opaque partition such that each eye of the practitioner can only see one image and the practitioner adjusts their own focus, however, to facilitate the viewing of a stereoscopic image by the practitioner(s), the prisms are preferably included to aid in the fusion of the images.

Turning now to FIGS. 3-8D, as noted, the ophthalmic device 10 is structured to obtain and transmit at least two images of at least one eye of a patient for the purpose of generating a stereoscopic image for the practitioner to view. "Stereoscopic" or "stereoscopy" as used herein refers to three-dimensional images, providing a perceived appearance of width, height, and depth as opposed to two-dimensional images that provide only width and height information. Moreover, in at least one embodiment the ophthalmic device 10 is a biomicroscope, such as a microscope used to study living tissue, and may incorporate a slit lamp, as described in greater detail hereinafter, for eye examination and diagnosis of certain eye conditions.

The ophthalmic device 10 minimally comprises an optic assembly 50 disposable in viewing relation to the eye of the patient and a processing assembly 60 disposable in operatively communicating relation to at least the optic assembly 50. More in particular, the optic assembly 50 is disposed in observing and image-obtaining relation to at least one eye of a patient, so as to collect image data of the eye and transmit this image data to the processing assembly 60. Accordingly, the optic assembly 50 can take the place of or supplement the binocular lenses in a traditional biomicroscope, capturing a magnified image of the eye rather than merely magnifying it for direct viewing. The processing assembly 60 is configured and disposable to receive image data from the optic assembly 50, and further comprises transmission capabilities operative to transmit the image data, such as to the control device 20 and display 21 via the network 30.

Figure 3:
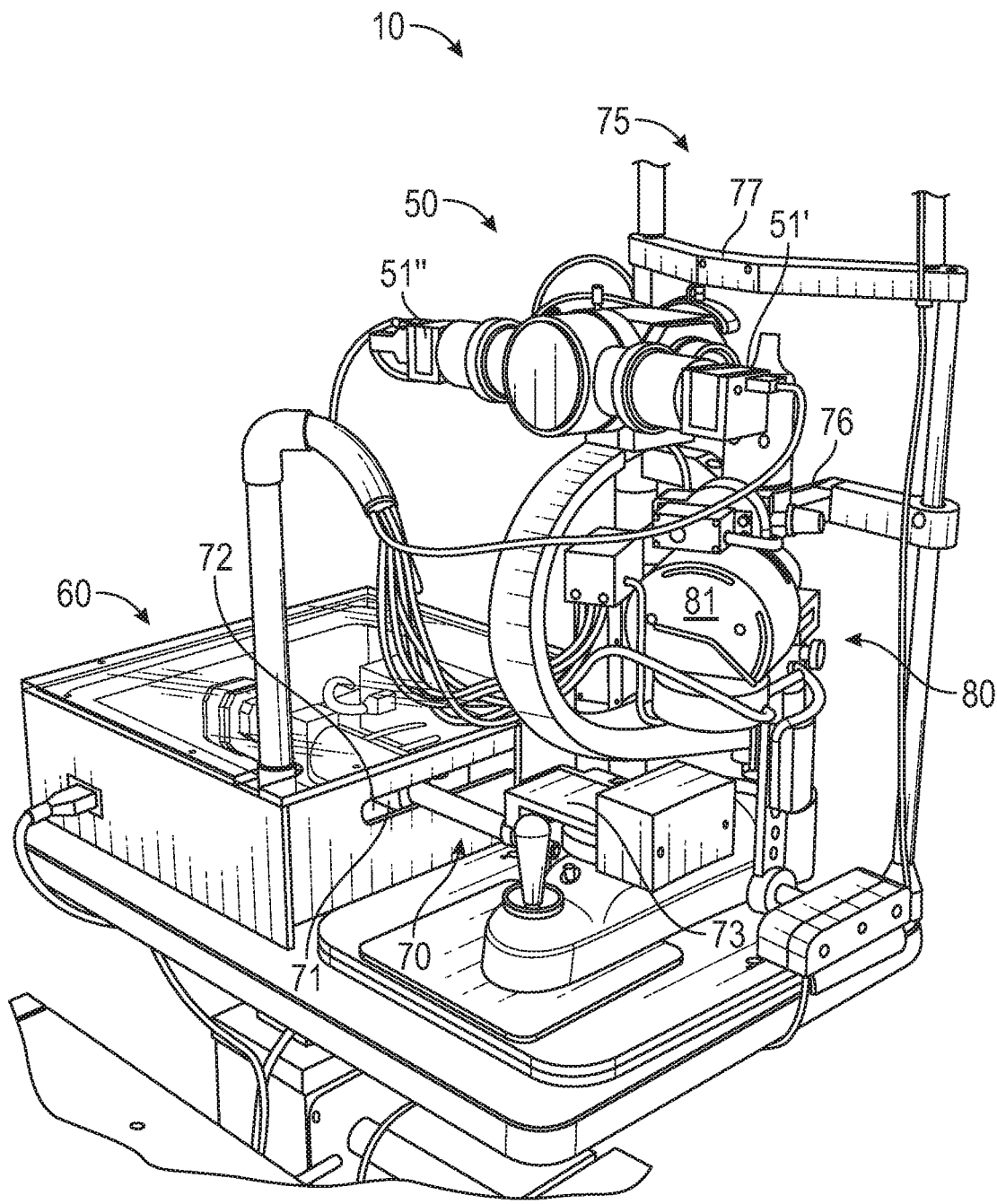
FIG. 3 is a perspective view of the ophthalmic device of the present system.

Specifically, and as shown in FIG. 3, the optic assembly 50 comprises at least one image capturing member 51 structured to receive, capture and/or obtain the image data of the eye of a patient. In at least one embodiment, the image capturing member 51 comprises a camera, such as a video camera, which may be digital and is preferably a high-definition camera capable of acquiring high-definition video of the eye. In embodiments, the resolution of the capturing member 51 can comprise of resolutions including 720p, 1080p, 4K, and 8K. By way of example only, the image capturing member 51 may be a high resolution half inch color CMOS camera (NT59-367, Edmund Optics, Barrington NJ), coupled to a 25 millimeter diameter, 50 millimeter focal length aspherized achromatic relay lens. An additional example of a comparable camera is model UI-1460SE-C from IDS, Woburn,MA It should be appreciated that the invention is not, however, limited to the above example, but can comprise any number of cameras and lenses appropriate for obtaining high resolution and/or stereoscopic images. Moreover, different sized cameras and relay lenses can be used in various embodiments. For example, to observe the entire eye of a patient when the Galilean telescope is set to give a maximum field of view, various heights (h) and focal lengths ($f_r$) of the relay lens are possible, as reported in the table below in millimeters:

TABLE 1

| h (mm) | $f_r$ (mm) |
|---|---|
| 32 | 36.8 |
| 31 | 37.9 |
| 30 | 39.2 |
| 29 | 40.6 |
| 28 | 42.0 |
| 27 | 43.6 |
| 26 | 45.2 |
| 25 | 47.0 |
| 24 | 49.0 |
| 23.52 | 50.0 |

Figure 5:
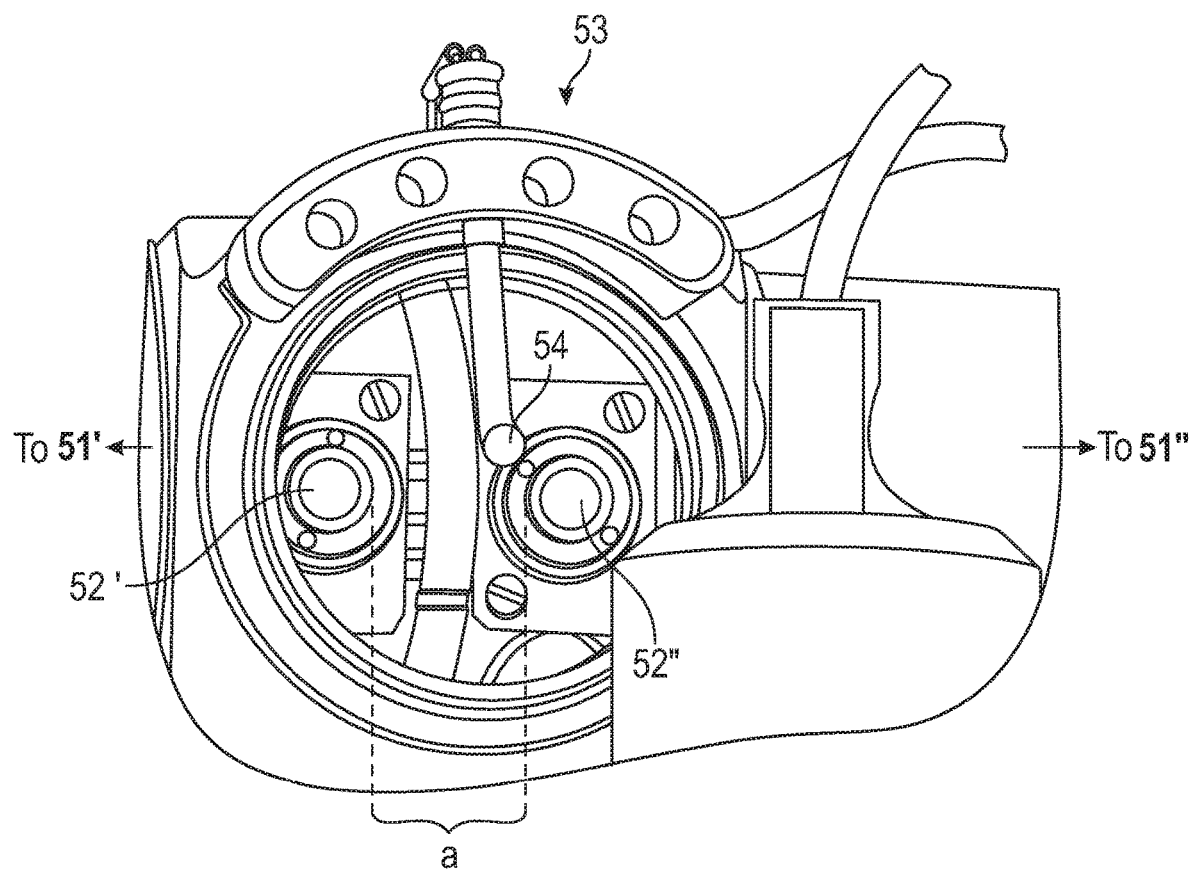
FIG. 5 is a perspective view of the optic assembly of the ophthalmic device of FIG. 3.

In at least one embodiment, the optic assembly 50 comprises a plurality of image capturing members 51, each disposed to obtain image data of the same eye from different perspectives, in order to allow for the generation of the stereoscopic image. For example, as shown in FIG. 3, the optic assembly 50 comprises a first image capturing member 51' and a second image capturing member 51", each disposed to receive image data of an eye from different objective lenses. As seen in FIG. 5, the optic assembly 50 comprises a first objective lens 52' and a second objective lens 52" disposed in facing relation to a patient, such that an image of a patient's eye enters the optic assembly 50 through the first and second objective lenses 52' and 52". The first and second objective lenses 52' and 52" are separated by a distance a, such as in the range of 21.7 millimeters to 21.9 millimeters, and preferably 21.8 millimeters, although other distances are possible as long as the images of the patient's eye may be obtained. In one embodiment, distance a is measured from the inner edges of the first and second objective lenses 52', 52".

In another embodiment, distance a is measured from the center of the first and second objective lens 52', 52". Thus, each objective lens 52 is positioned at a different distance from particular areas of the eye, such that the image data entering the first objective lens 52' will be slightly different from the image data entering the second objective lens 52". This enables a stereoscopic image to be produced and viewed.

The optic assembly 50 may further comprise at least one beam splitter, such as a Zeiss prismatic beam splitter, structured to redirect the light, and therefore image data, entering the first and second objective lenses 52', 52" to the first and second image capturing members 51', 51", respectively, for image data capture and transmission. In this manner, the image capturing member 51 can be said to be interactive with the objective lens 52 to capture the image data of an eye. Accordingly, the first image capturing member 51' will capture and transmit a slightly different image from that captured and transmitted by the second image capturing member 51", thus creating a stereoscopic image.

Figure 4:
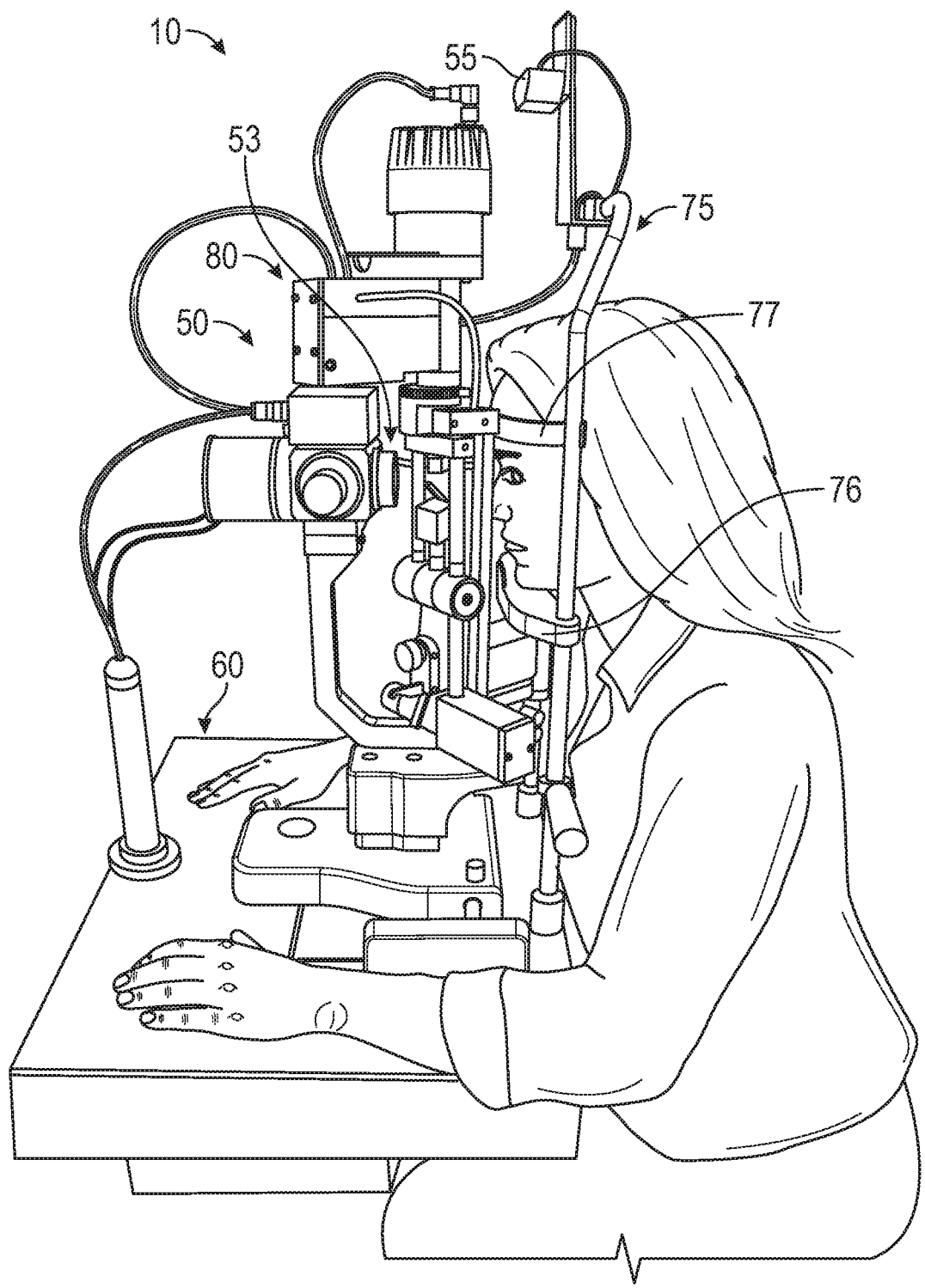
FIG. 4 is a perspective view of an example embodiment of an ophthalmic device.
Figure 15:
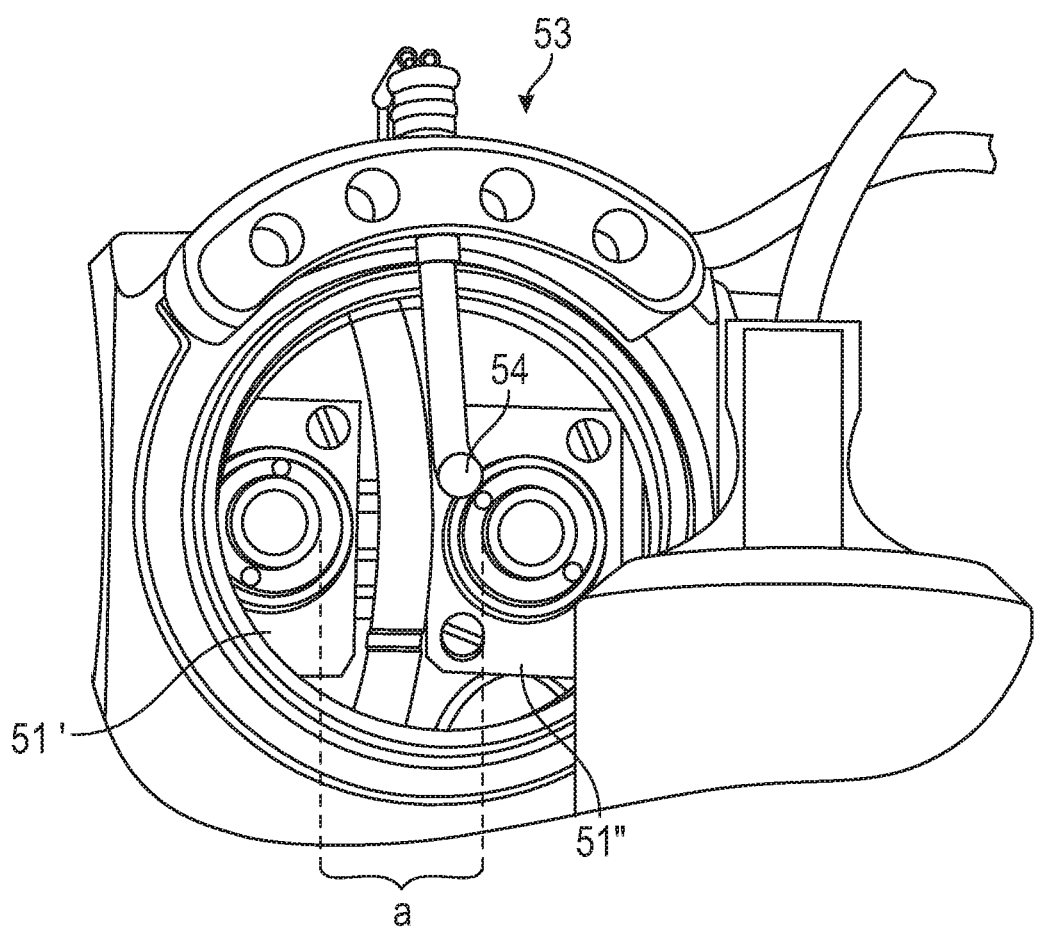
FIG. 15 is a perspective view of the optic assembly of the ophthalmic device of FIG. 4.

FIG. 4 is a perspective view of an example embodiment of an ophthalmic device and FIG. 15 is a perspective view of an embodiment of the optic assembly of the ophthalmic device of FIG. 4. In the embodiment, the optical assembly 50 is positioned in line with the patient's optical path, removing the need for a beam splitter. As camera technology develops, cameras are becoming smaller and increasing in image resolution capturing abilities. These smaller cameras can provide for a variety of positioning layouts that lead to improve performance of the optic assembly 50. For example, the optic assembly 50 can have the first and second capturing members that can be dual subminiature high resolution cameras, disposed within the direct or full optical pathway of image data. By position the capturing members in the direct optical pathway, there is no need for the use of the beam splitter, and there is less potential of image quality loss.

Further, in embodiments wherein the image capturing members 51 are high-definition cameras, each image capturing member 51', 51" obtains and transmits high-definition images, which may be encoded and/or multiplexed for more efficient transmission, and which may be combined at the ophthalmic device and/or at the display 21, although as noted, in an embodiment each image is maintained separate and displayed independently such that a three-dimensional image is attained by a fusion technique using the appropriate viewer. This is an advantage over currently known devices since the resolution of the high-definition image data from each image capturing member 51 is maintained, thereby preserving the high integrity of the image data, as opposed to currently known devices that cut the resolution of image data in half, reducing image quality. Accordingly, the present system 100 permits a higher degree of quality and contrast in the live stereoscopic images, which enables accurate examination, stereopsis, and diagnosis. Specifically, the high-definition stereoscopic live image data of the present system 100 allows for a practitioner to, by way of example only and not limiting in any way: discern details in the structure of the eyelid, eyelashes, conjunctiva, limbus, cornea, anterior chamber, cells, flare, the iris, crystalline lens or artificial lens in the case of patients with cataract extraction and intraocular lens (IOL) implantation; discriminate particle aggregates; determine abnormal cells, abnormal growth such as in the case of nevus, tumors, and any thickness abnormalities in the tissues; identify plasma or hemorrhages and other moieties; discern damaged structures in the depth of an eye's transparent tissues, such as the cornea, anterior chamber, and lens; determine iris and cornea touch by the proximal tube of a glaucoma drainage implant; assess the post-operative status and health of implants, such as corneal transplants, supra or intracorneal implants, and keratoprostheses; differentiate between retroprosthetic membranes and membranes developing across the anterior chamber, such as from the trabecular meshwork or iris; and assess the extent of anterior and posterior capsule opacification. Accordingly, the present system 100 permits a higher degree of quality and contrast in live stereoscopic images, which enables good stereopsis and, therefore, accurate examination and diagnosis.

As shown in FIGS. 4 and 15, the optic assembly 50 further comprises a fixation assembly 53 having directing capabilities to direct and maintain a patient's visual focus, so as to position the patient's eye appropriately for examination. To this end, the fixation assembly 53 comprises at least one light source 54 disposable to direct a patient's eye during use. In one example, the light source 54 is a light emitting diode (LED), although other embodiments contemplate other types of light sources. The light source 54 is structured to emit light in the visible range and can emit light in any of a variety of colors and color temperatures. Some patients may suffer from debilitating photosensitivity. The light source 54 can be adjusted to a specific intensity in kelvin or by selecting from preset light emulation modes that's vary from warm incandescent to a cooler fluorescent. In some embodiments, the light source 54 emits light in a constant, uninterrupted fashion. In other embodiments, the light source 54 emits light in discreet packets, such as in flashes, bursts, or blinking fashion, and may emit light in a particular pattern. Further, in some embodiments, the fixation assembly 53 comprises a plurality of light sources 54 such as multiple LED emitters or in other words the light source 54 may be a screen with multiple pixels, in which the various light sources 54 are structured to emit light of different colors and/or at different times, and/or in different locations, such as in a pattern and/or in different positions and locations, in order to facilitate the examination and direct the patient's eye to different positions during the examination, thus enabling a view of different portions of the eye. In an embodiment the light source 54 is able to be moved and repositioned to facilitate the examination and direct the patient's eye to different positions during the examination, thus enabling a view of different portions of the eye. In another embodiment the fixation assembly 53 includes a projection system that is controlled by the practitioner and can project a fixation dot that can be oriented in 360 degrees in the patient's visual field. As the practitioner controls the location of the fixation dot, a computer-synthesized voice can instruct the patient to fixate in the corresponding quadrant. The computer-synthesized voice can be generated in multiple languages and may be selected to be the native language of the patient.

Figure 6:
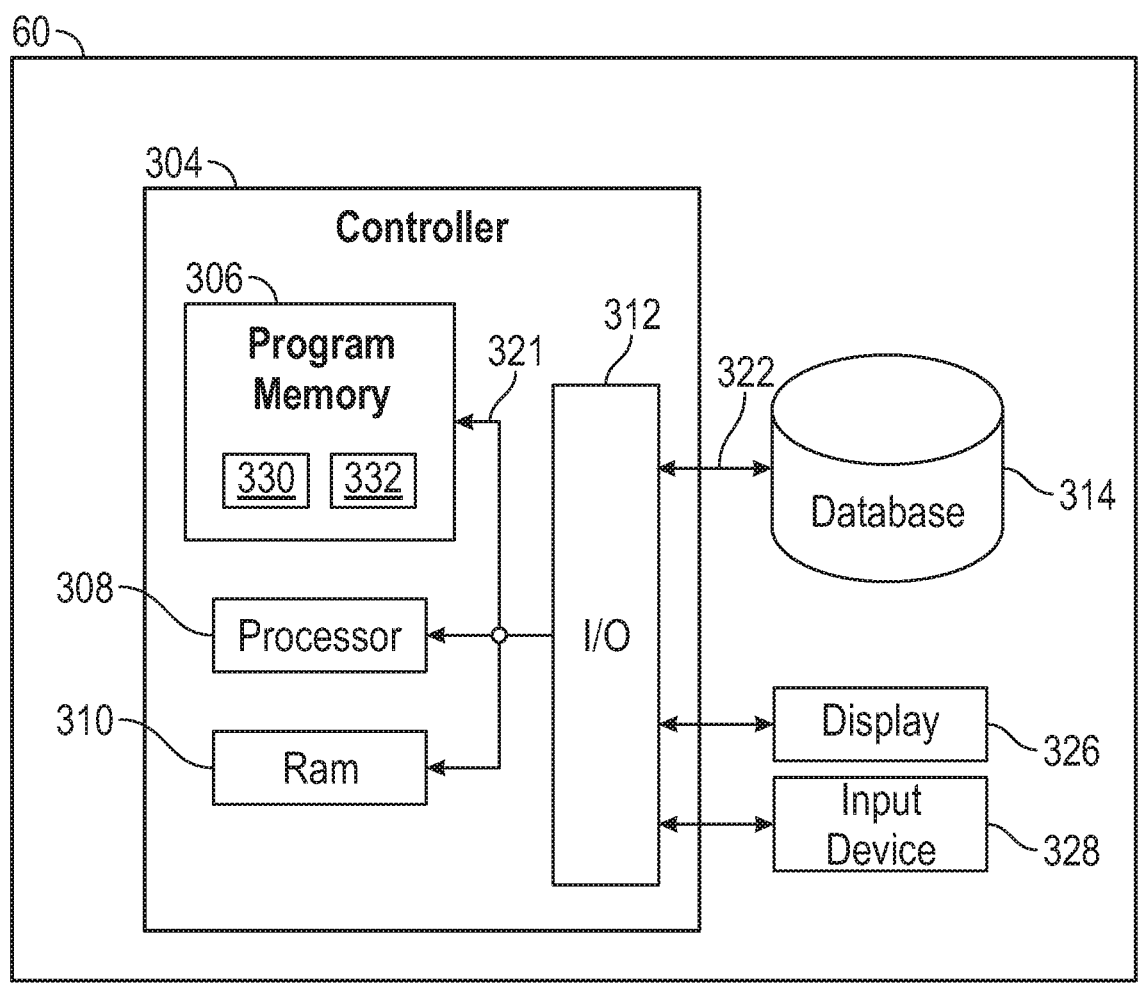
FIG. 6 is a functional block diagram of a processing assembly.

FIG. 6 is a functional block diagram of a processing assembly. Accordingly, in at least one embodiment the processing assembly 60 comprises a controller 304 operatively connected to a database 314 via a link 322 connected to an input/output (I/O) circuit 312. It should be noted that, while not shown, additional databases 314 may be linked to the controller 304 in a known manner. Furthermore, these databases 314 may be external to the processing assembly 60.

The controller 304 includes a program memory 306, a processor 308 (may be called a microcontroller or a microprocessor), a random-access memory (RAM) 310, and the input/output (I/O) circuit 312, all of which are interconnected via an address/data bus 321. It should be appreciated that although only one microprocessor 308 is shown, the controller 304 may include multiple microprocessors 308. Similarly, the memory of the controller 304 may include multiple RAMs 310 and multiple program memories 306. Although the I/O circuit 312 is shown as a single block, it should be appreciated that the I/O circuit 312 may include a number of different types of I/O circuits. The RAM 310 and the program memories 306 may be implemented as semiconductor memories, magnetically readable memories, non-volatile memories, and/or optically readable memories, for example.

The program memory 306 and/or the RAM 310 may store various applications (i.e., machine readable instructions) for execution by the microprocessor 308. For example, an operating system 330 may generally control the operation of the processing assembly 60 and provide a user interface to the processing assembly 60 to implement the processes described herein. The program memory 306 and/or the RAM 310 may also store a variety of modules 332 for accessing specific functions of the processing assembly 60. By way of example, and without limitation, the modules 332 may include, among other things: operating the ophthalmic device 10, converting and transmitting data from the ophthalmic device 10 to the control device(s) 20 at any of a plurality of locations, for receiving, converting, and relaying control messages from the control device(s) 20 to the appropriate component parts of the ophthalmic device 10, and as needed, to provide control feedback to the control device(s) 20. In other examples, the modules 332 may further generate a visual representation of the image data and ophthalmic device 10 inform ad on and display the visual representation on the control device 20.

The modules 332 may include software to execute any of the operations described herein. The modules 332 may include other modules, for example, implementing software keyboard functionality, interfacing with other hardware in the processing assembly 60, etc. The program memory 306 and/or the RAM 310 may further store data related to the configuration and/or operation of the processing assembly 60, and/or related to the operation of one or more modules 332. For example, the data may be data determined and/or calculated by the processor 308, etc.

In addition to the controller 304, the processing assembly 60 may include other hardware resources. The processing assembly 60 may also include various types of input/output hardware such as the visual display 326 and input device(s) 328 (e.g., keypad, keyboard, microphone etc.). The input device(s) 328 may include sensors such as light intensity sensors, temperature sensors, and humidity sensors. In an embodiment, the display 326 is touch-sensitive, and may cooperate with a software keyboard routine as one of the software modules 332 to accept user input. It may be advantageous for the processing assembly 60 to communicate with a broader network (not shown) through any of a number of known networking devices and techniques (e.g., through a computer network such as an intranet, the Internet, etc.). For example, the processing assembly 60 may be connected to a database 314 of preset positioning values that can be used to position the ophthalmic device 10 based on a patients electronic record.

In addition, the processing assembly 60 may be connected to a database 314 of preset positioning values that operate sequentially to position the ophthalmic device 10, control one or more functions of the ophthalmic device 10, and record one or a plurality of sequences of images without further intervention from the practitioner. As a corollary, the sequence of operations may be divided into one or a plurality of separate sequences, where such a sequence is initiated automatically, upon initiation of the patient, or upon initiation of the practitioner. Such pre-defined sequences of operations may simplify the control for common examination workflows, and may further reduce the need for expert intervention in operating even the remotely operated device.

In yet another embodiment, the sequence of operations of the imaging system applied during one patient examination are stored in a database 314, and applied in a subsequent patient examination. For example, the first sequence may be recorded during a practitioner's examination of a patient, responsive to specific clinical observations relevant to the patient. Subsequent examinations that repeat the initial examination assure that the same clinical observations may be made. Further still, the application of a first sequence of operations to a group of patients may assure that all the patients receive a similar degree of care, while allowing subsequent imaging to be managed without the direct interaction of the practitioner.

The processing assembly 60 can be in electrical communication with the positioning assembly 70, the patient positioning assembly 75, the slit assembly 80, and the optic assembly 50. The processing assembly 60 can be configured to receive the position of the patient. The processing assembly 60 can transmit control messages to the patient positioning assembly 75 to control the position of the chin rest 76 and head rest 77 with regards to the position of the patient. In other embodiments, the processing assembly 60 may comprise a plurality of computers and/or computing devices cooperatively disposed to maintain and transmit real-time image data and receive and relay control messages, as well as power the ophthalmic device 10. For instance, in one embodiment a plurality of computing devices comprising the processing assembly 60 are multi-threaded to split the computational requirements among resources and thus speed the generation, processing and/or transmission of the real-time high definition images, while also achieving substantially real-time control of the parameters of the ophthalmic device 10 without any lag or delay. Indeed, in another embodiment, the processing assembly 60 can comprise hyper-threading technology to disperse the multiple processes.

The power supply of the processing assembly 60 provides the power to run and operate the ophthalmic device 10. In at least one embodiment the processing assembly 60 comprises a power stabilizing assembly including a sine wave converter and batteries. By way of example only, the power stabilizing assembly comprises a 1500 W pure sine wave converter (S1500-112B22, DonRowe Co., Monroe OR) and a plurality of 12V deep cycle batteries (D34M, Optima Batteries Co., Milwaukee, WI). Also, the power stabilizing assembly can include four deep cycle batteries. Accordingly, the power stabilizing assembly is structured to maintain constant power to the ophthalmic device 10, even in remote locations where the power supply may be unstable, such as in a tactical location and/or an under developed location. The power stabilizing assembly can also include a battery charger, such as a heavy duty battery charger (PM-42020, TurtleMarine.com Ltd., New York NY), which can be used in conjunction with a local AC supply to recharge the batteries. To further accommodate to the varying electric infrastructure found on each continent, the processing assembly 60 can be integrated with a smart sensing power supply that can be operable auto adjust to the electrical source it is connected to.

The processing assembly 60 is configured and disposable in receiving relation to data from the rest of the ophthalmic device 10, such as the image data from the optic assembly 50. For example, in at least one embodiment the processing assembly 60 and the at least one image capturing member 51 are connected by a cable to facilitate the transmission of image data from the image capturing member 51 to the processing assembly 60. Such connection cable has specifications sufficient for the rapid transmission of large amounts of data, such as high definition video. Moreover, in embodiments having a plurality of image capturing members 51', 51", each image capturing member 51', 51" connects to the processing assembly 60 independently. In one embodiment, each image capturing member 51', 51" connects separately to the processing assembly 60, although in other embodiments they may be connected in series or combined for unified transmission before being received in the processing assembly 60.

Preferably the processing assembly 60 includes a video encoder structured to combine the image data from the image capturing member(s) 51, 51', 51" as well as other data, such as video and/or audio data from an external data capturing member 55, discussed in greater detail hereinafter, and an interface 23 into a single multiplexed stream. As used herein, "multiplexing" means the sending of multiple signals or streams of information on a carrier at the same time in the form of a single complex signal. In one embodiment, the video encoder comprises a CUBE-200 (Teradek, Irvine CA) using a H.264 High Profile (Level 4.1) video compression and including a video scaler to convert from 1080 to 720, 480, or 240 resolutions. In another embodiment the video encoder is a software encoder.

Accordingly, once compressed, multiplexed, and/or encoded, the image data is transmitted by the processing assembly 60 to the control device(s) 20, where it is presented on the associated display 21. Alternately, however, depending upon the available bandwidth and/or transmission capacity of the network, the image data from the image capture member(s) 51 can simply be transmitted by the processing assembly 60 as it is received. Regardless of the embodiment, however, the processing assembly 60 transmits in the aforementioned image data in real-time. To this end, in at least one embodiment, the transmission capabilities of the processing assembly 60 comprise an end-to-end latency, or lag time, of approximately one-eighth to one half of a second and facilitate the transmission of high-resolution image data at a bit rate in the range of about 2 to 4 megabytes per second. In another example, the transmission capabilities of the processing assembly 60 facilitate the transmission of standard definition resolution image data, such as at a bit rate of approximately one megabyte per second or less. It should be appreciated that the above are approximate rates and times, and may vary slightly above or below the stated outer limits, such as by ±10 kilobytes per second or 5%. Moreover, the transmission capabilities of the processing assembly 60 are configured to transmit the image data, such as in a high-definition multiplexed signal, over the network 30 in the plurality of modes previously described, such as over the network 30 via satellite, Wi-Fi, wired Ethernet, wireless Ethernet, cellular connection such as 3G, 4G, or 5G and other wireless connections.

In order to effectively receive and interpret the control messages, the processing assembly 60 further comprises receiving capabilities. Similar to the transmission capabilities which provide the image data and feedback as needed, and by way of example only, the receiving capabilities of the processing assembly 60 are configured to receive control messages via satellite, Wi-Fi, wired Ethernet, wireless Ethernet, cellular connection such as 4G, and other wireless connections. Once received, the processing assembly 60 relays the control messages to the appropriate component of the ophthalmic device 10 for which the control message is intended. For example, in at least one embodiment the relay capabilities of the processing assembly 60 relay control messages and other information to the various components of the positioning assembly 70 and slit assembly 80. Accordingly, the processing assembly 60 is disposed in interconnecting relation to the positioning assembly 70 and slit assembly 80, such as by a cable or other structure capable of transmitting data and information. In at least one embodiment, the relay capabilities comprise a microcontroller, such as, and by way of example only, a BASIC stamp development board (Parallax, Rocklin, California) with 24-pin BASIC stamp module and programmed with PBASIC. In one embodiment, the BASIC stamp module has 32 bytes of RAM and a processor speed of 50 megahertz, although these and all parameters can vary as optimal for miniaturization, portability or increased processing, and/or as may be dictated by advances in technology.

As another example, if necessary the processing assembly 60 can include a digital to analogue (D/A) converter configured to convert digital output from the control device 20, such as control messages, into analog input for the DC/AC converter, which converts from frequency to voltage for a DC/AC controller such as the one discussed hereinafter.

Among the components operable by control messages are a positioning assembly 70 and its component parts which are operative to adjust the position of the slit assembly 80, the optic assembly 50, and the patient positioning assembly 75 of the ophthalmic device 10 in a plurality of dimensions, and more specifically, in three-dimensions: laterally, vertically, and orthogonally (nearer or further a patient). As such, the positioning assembly 70 preferably comprises a first positioning member 71 coupled to the slit assembly 80 and the optic assembly 50. The first positioning member 71 structured and disposed to position components of the ophthalmic device 10 in a plurality of operative orientations along an x-axis and a y-axis. As used herein, "x-axis" refers to the axis or imaginary line that runs lateral to the ophthalmic device 10 and the patient when situated in front of the ophthalmic device 10. The first positioning member 71 therefore is structured to move the slit assembly 80, the optic assembly 50, and other components of the ophthalmic device 10 laterally, or in a side-to-side fashion. The "y-axis" as used herein refers to the axis or imaginary line that runs depth-wise with respect to the ophthalmic device 10 and the patient when situated in front of the ophthalmic device 10. The first positioning member 71 therefore is structured to move the slit assembly 80, the optic assembly 50, and other components of the ophthalmic device 10 forward and back, such as closer or further from a patient during examination. Accordingly, the x-axis and y-axis collectively define a first plane disposed in lateral relation to the ophthalmic device 10 and perpendicular to a patient situated in front of the ophthalmic device 10.

In at least the embodiment of FIG. 3, the first positioning member 71 comprises an elongate configuration and is structured to adjust, such as telescopically, in order to create movement along the x-axis. In addition, the first positioning member 71 is preferably fixedly secured at one end to components of the ophthalmic device 10 and at another location to a support structure such as a housing of the processing assembly 60 so that movement of the first positioning member 71 effects a change in the lateral position of components of the ophthalmic device 10. Accordingly, since the first positioning member 71 is interconnected to the slit assembly 80, the optic assembly 50, and other components of the ophthalmic device 10, movement of the first positioning member 71 in a front-to-back direction similarly effects movement and positioning of the slit assembly 80, the optic assembly 50, and other components of the ophthalmic device 10 along a y-axis.

To facilitate movement of the slit assembly 80, the optic assembly 50, and other components of the ophthalmic device 10 along the x- and y-axes, the positioning assembly 70 further comprises a positioning aperture 72 disposed along a side of the processing assembly 60 facing the ophthalmic device 10 and in receiving relation to the first positioning member 71 which extends through the aperture 72. Further, the positioning aperture 72 is dimensioned to provide the boundaries of movement of the first positioning member 71 along the x- and y-axis.

The positioning assembly 70 also comprises a second positioning member 73 structured and disposed to position the slit assembly 80, the optic assembly 50, and other components of the ophthalmic device 10 in a plurality of operative orientations along a z-axis. As used herein, the "z-axis" refers to the axis or imaginary line that runs vertically with respect to the ophthalmic device 10 and the patient when situated in front of the ophthalmic device 10. Accordingly the z-axis defines a second plane that lies parallel to front face of the ophthalmic device 10 which is disposed nearest a patient during examination. In other words, the second positioning member 73 is structured to raise and lower the slit assembly 80, the optic assembly 50, and other components of the ophthalmic device 10. The second positioning member 73 can be operable to accommodate the anatomical variety of the human head and eye position by having a range of motion that is suitable for adults down to pediatric patients.

The first positioning member 71 and second positioning member 73 are each preferably connected to different motors that respond to control messages from the control device 20 and drive motion in each of the three-directions. For instance, the first positioning member 71 connects to a stepper motor that controls lateral movement along the x-axis. In one embodiment, a NEMA 17 stepper motor and linear stage (D-A. 083-HT17-4-1NO-B/4 "The Digit", Ultra Motion Inc., Cutchogue NY) capable of producing up to 75 pounds of thrust and having a resolution of 0.00004 inches per step and a range of 4 inches is used as the stepper motor for x-axis movement. In another embodiment, the stepper motor is a NEMA 23 stepper motor. Further, in one embodiment, the stepper motor is driven by a stepper motor encoder (EZHR17EN, All Motion Inc., Union City CA). A stepper motor controller, such as a NEMA 17 stepper motor controller, having dual encoders and structured to operate from 12 volts to 40 volts, is secured to the stepper motor.

The first positioning member 71 also connects to a stepper motor controlling the front-and-back, or orthogonal, motion along a y-axis. For example, in one embodiment, a NEMA 17 stepper motor and linear stage (ET-100-2 "e-Track", Newmark Inc., Mission Viejo CA) capable of carrying a 10 pound load and having a resolution of 0.000009 inches per step in a range of 2 inches is provided. The stepper motor for y-axis movement is driven by a stepper motor encoder, such as previously described.

A servo interconnects the second positioning member 73 with a slit height adjustment member 85, discussed in greater detail below.

This servo controls the vertical movement of the slit assembly 80, the optic assembly 50, and other components of the ophthalmic device 10. In one embodiment, the servo (HS-7950TH, Hitec RCD USA Inc., Poway CA) is part of a friction based system in which a friction member, such as rubber tire, is disposed around the servo actuator. Moreover, the vertical movement servo comprises a potentiometer, such as model 312-9100F-5K (Mouser Electronics, Mansfield TX) which is secured to the ophthalmic device 10 and provides mechanical stops at the limits of the stage of the ophthalmic device 10 while permitting continuous rotation there between. In such an embodiment, based on the diameter of the friction member and the diameter of the servo gear, such as 2.5 inches, the servo comprises a gear ratio of approximately 1:7. Accordingly, the vertical movement servo provides for slight movement along the z-axis. This servo is also driven by the microcontroller of the processing assembly 60.

Figure 7:
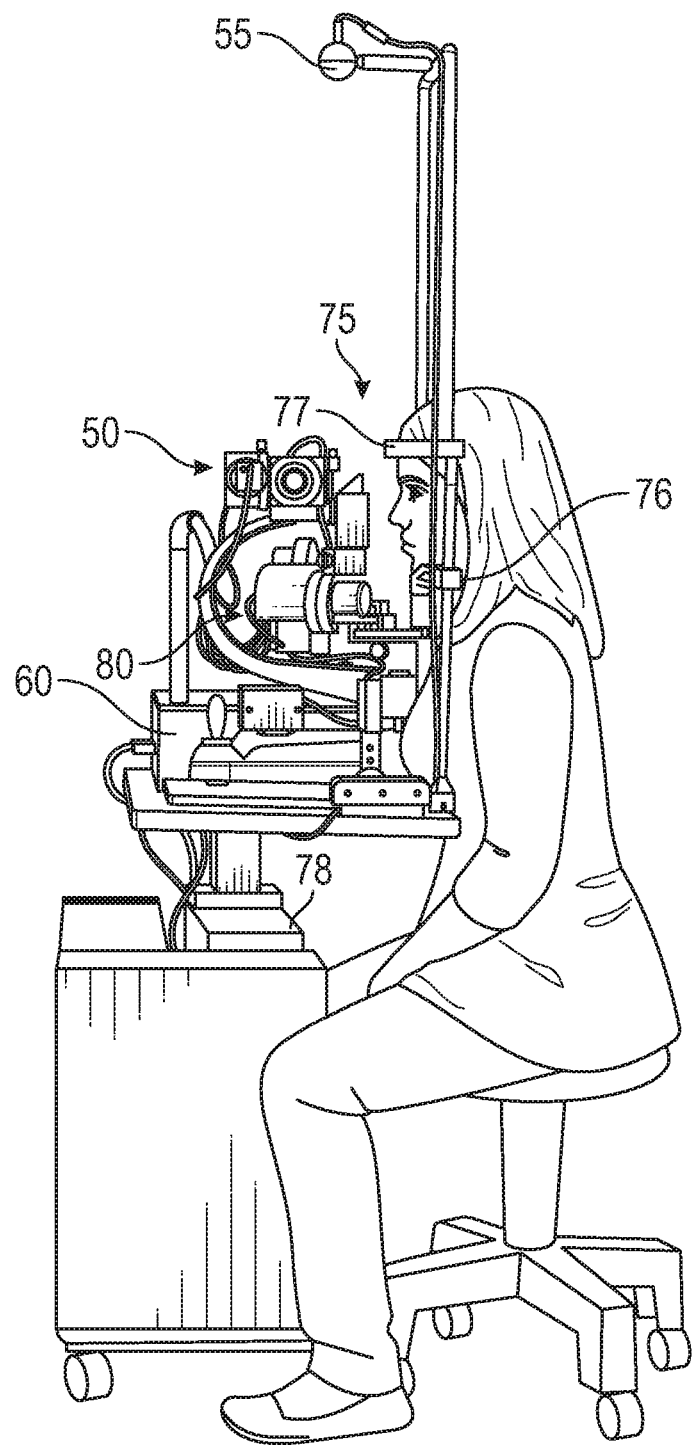
FIG. 7 is a side view of the ophthalmic device of FIG. 3 disposed in relation to a patient.

As shown in FIGS. 3, 4, and 7, the positioning assembly 70 further comprises a patient positioning assembly 75 structured and disposed to appropriately place a patient in relation to the ophthalmic device 10 for examination. For instance, the patient positioning assembly 75 comprises a chin rest 76 configured to receive and support the chin of a patient, and thereby position the patient's eye in the approximate area of the optic assembly 50. Fine-tuned positioning for image collection is subsequently achieved by the first and second positioning members 71, 73 described previously. The patient positioning assembly 75 further comprises a head rest 77 disposed above the chin rest 76 and configured to support the forehead of a patient so as to stabilize the patient's head and minimize superfluous movement during examination. In at least one embodiment, the patient positioning assembly 75 is disposable for use with a patient lying in a supine position, rather than sitting up as in FIGS. 4 and 7, and attaches to the ophthalmic device 10 accordingly.

In at least one embodiment, as shown in FIGS. 4 and 7, the patient positioning assembly 75 further comprises an external data capturing member 55 disposable to obtain positional data, such as image data, of the patient in relation to components of the ophthalmic device 10, preferably disposed above the patient. In an embodiment the external data capturing member 55 is positioned above the head rest 77. In at least one embodiment, the external data capturing member 55 comprises a video camera, and may take high-definition or standard-definition resolution video, as defined previously. The external data capturing member 55 may be operable to zoom in and out to facilitate the positioning of the patient. With the use of the external data capturing member 55 the patient can be guided into position without requiring the practitioner to touch the patient. The external data capturing member 55 can also comprise audio capabilities to capture audio data from the patient, such as verbal responses to questions from remotely located practitioner(s), in addition to video data. For example, in one embodiment, the external data capturing member 55 comprises a web camera (Blue Microphones Inc., Weatlake Village CA) having a 2 megapixel sensor and a condenser capsule for high quality sound with a frequency response in the range of 35 Hertz to 20 kiloHertz and a sample/word rate of 44.1 kiloHertz per 16 bits. Accordingly, the external data capturing member 55 is structured to obtain additional information about the patient, such as their position in relation to components of the ophthalmic device 10, as well as enable verbal communication with the patient.

In an embodiment the patient positioning assembly 75 can be operable to auto-adjust the chin rest 76 and the head rest 77 by utilizing at least the external data capturing member 55 to properly position the patient's eyes in the optical path. The auto-adjustments can be performed continually or triggered throughout the examination to maintain correct alignment. For example as a patient adjust their posture, the patient positioning assembly 75 can adjust and maintain the optical path with the patient's eyes without requiring manual practitioner control. Furthermore, the chin rest 76 and head rest 77 can include integrated sensors for detecting repositioning of the patient and that can be used to alert the practitioner of deviations greater than the set tolerances and/or can trigger an automated voice command to the patient to correct the posture deviation.

As shown in FIG. 7, the positioning assembly 70 can also further comprise an audio member 78 structured and operative to transmit and provide sound to the patient. For example, in one embodiment, the audio member 78 comprises at least one speaker through which verbal directions and questions from the practitioner(s) located at the control device(s) 20 at disparate predetermined locations can be communicated to the patient. For instance, based at least in part on image data provided by the external data capturing member 55, as well as from the image capturing member(s) 51, a practitioner(s) may be able to determine if a patient should move his or her head in a particular direction for better imaging of the eye and direct the patient accordingly, instruct the patient to look in a particular direction(s), instruct the patient not to blink, ask the patient questions, etc. In an embodiment the control device 20 is operable to convert the voice commands of the practitioner and convert the commands to the patient in their preferred language through the audio member 78. Similarly the control device 20 is operable to convert the voice commands of the patient and convert the commands to the practitioner in the practitioner's preferred language. In an alternative embodiment the processing assembly 60 is operable to convert the voice commands of the practitioner and convert the commands to the patient in their preferred language. Similarly the processing assembly 60 is operable to convert the voice commands of the patient and convert the commands to the practitioner in the practitioner's preferred language.

The audio member 78 is configured to relay this verbal information to the patient so they may respond according to the practitioner's instructions and provide answers to questions posed by the practitioner.

As shown in FIGS. 3, 4, 7 and 8A-8D, the ophthalmic device 10 further comprises a slit assembly 80 structured and collectively disposed to adjust at least one dimension of a slit and to adjust the magnification of the ophthalmic device 10. For example, in at least one embodiment the slit assembly 80 comprises a slit lamp that is coupled to a biomicroscope for examination of a patient's eye. "Slit lamp" as used herein refers to a slit lamp instrument commonly used in conjunction with a biomicroscope for eye examination as those of ordinary skill in the art will readily appreciate. Preferably, the slit assembly 80 comprises a slit lamp light source 81, at least one slit adjustment member, and a slit lamp magnification control 82. The slit lamp light source 81 is a source of illumination and is disposed within the slit assembly 80 and in light-directing relation to the eye of a patient. The light produced by the slit lamp light source 81 is therefore directed through the slit assembly 80 and components of the ophthalmic device 10 to shine upon the eye of a patient sitting in front of the ophthalmic device 10 during examination, as shown in FIGS. 4 and 7, thereby illuminating the various parts of the eye, including the eyelid, eyelashes, conjunctiva, limbus, cornea, anterior chamber, iris, and lens of the eye. The light reflects off these various components of the eye and back into the ophthalmic device 10 through the objective lenses 52', 52", providing image data of the eye. Further, a slit lamp intensity control 83 is provided, such as within the housing of the processing assembly 60, and is structured to control the intensity of light emitted from the slit lamp light source 81. In at least one embodiment, a DC/AC converter, such as model MCPC1225A (Crydom Co., San Diego CA) controls and/or limits the slit lamp intensity control 83. For example, the DC/AC controller is a control relay with 40-140 volts of alternating current (AC), a rated current of 35 amps, and a proportional load voltage input of 0-5 volts in direct current (DC). The DC/AC control relay is disposed within the processing assembly 60 and in driven relation to the microcontroller. Accordingly, the processing assembly 60 directs the intensity of the slit lamp intensity control 83 and therefore, the intensity of the light used in the slit lamp and ophthalmic device 10. Further, since control messages from the control device 20 are directed to the slit lamp intensity control 83, which are received and relayed by the processing assembly 60, a practitioner(s) at the control device(s) 20 can control and direct the intensity of the light used in the slit lamp during examination.

In an embodiment, the slit lamp light source 81 comprises an LED illumination system that is operable to adjust the intensity of the light produced incrementally using a digital slide on the display 21 for micro adjustments. In an embodiment the interface 23 includes controls for adjusting the intensity of the light produced by the slit lamp light source 81. In additional, the practitioner can select from pre-set intensities for quick and consistent adjustments.

Figure 8A:
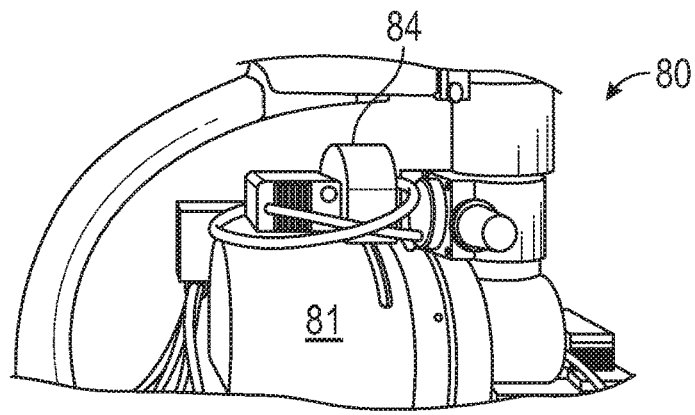
FIG. 8A is a perspective view of the slit width adjustment member of the slit assembly of the ophthalmic device of FIG. 3.

Moreover, the slit assembly 80 preferably comprises at least one slit adjustment member to vary at least one dimension of the slit of the slit assembly 80. As is readily understood by those of ordinary skill in the art, the slit of a slit lamp is an aperture through which the light of the slit lamp passes. The width, height, and angle of the slit may be varied to control the amount of light, dimension, and direction of the beam of light issuing from the slit lamp, so as to maximize the efficiency and accuracy of an eye examination. Accordingly, as shown in FIG. 8A, the slit assembly 80 of the present invention comprises a slit width adjustment member 84 structured to adjust a lateral dimension (width) of the slit of the slit assembly 80. In at least one embodiment, the slit width adjustment member 84 comprises a gear system coupled to a dedicated servo motor, such as model HS-805BB (Hitec RCD USA Inc., Poway CA) having a three pole motor, dual ball bearing, and capable of generating a maximum torque of 343 ounce*inch, and is further disposed to physically adjust the width of the slit. For example, only 60° of rotation is required to adjust the slit width. Accordingly, the gear assembly of the slit width adjustment member 84 comprises an 84-teeth gear wheel attached to the servo which matingly engages the teeth of a partial gear wheel which, if whole, would have 114 teeth, thereby providing a gear ratio of 1:1.357. The slit width adjustment member 84 is securely fastened to the gear wheel. The servo is mounted to the slit lamp assembly 80. Accordingly, movement of the servo rotates the servo gear wheel, in turn rotating the partial gear wheel within 60° of rotation, thereby driving the slit width adjustment member 84 and correspondingly producing a narrowing or widening of the slit width. Moreover, the dedicated servo for the slit width adjustment member 84 is controlled by the processing assembly 60, such as a microcontroller, and is structured to respond to control messages from the control device 20. Accordingly, a practitioner at a control device 20 can control and direct the adjustment of the slit width.

Figure 8B:
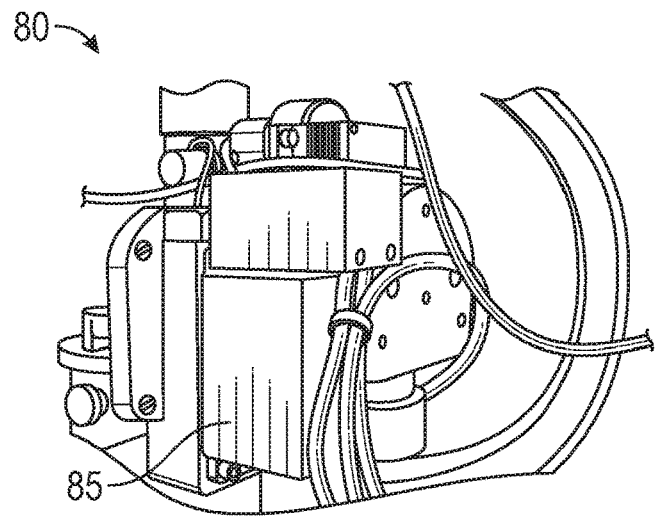
FIG. 8B is a perspective view of the slit height adjustment member of the slit assembly of the ophthalmic device of FIG. 3.

As shown in FIG. 8B, the slit assembly 80 of the present invention also may comprise a slit height adjustment member 85 structured to adjust a vertical dimension (height) of the slit of the slit assembly 80. In at least one embodiment, the slit height adjustment member 85 comprises a gear system coupled to a dedicated servo motor, such as model HS-7950TH (Hitec RCD USA Inc., Poway CA) having a coreless motor, dual ball bearing, and capable of generating a maximum torque of 486 ounce*inch, and is further disposed to physically adjust the height of the slit. For example, only 135° of rotation is required to adjust the slit height. Accordingly, the gear assembly of the slit height adjustment member 85 comprises an 80-teeth gear wheel attached to the servo which matingly engages the teeth of a partial gear wheel which, if whole, would have 94 teeth, thereby providing a gear ratio of 1:1.175. The slit height adjustment member 85 is securely fastened to the gear wheel. The servo is mounted adjacent to the slit lamp assembly 80. Accordingly, movement of the servo rotates the servo gear wheel, in turn rotating the partial gear wheel within 135° of rotation, thereby driving the slit height adjustment member 85 and correspondingly producing a lengthening or shortening of the slit height. Moreover, the dedicated servo for the slit height adjustment member 85 is controlled by the processing assembly 60, such as a microcontroller, and is structured to respond to control messages from the control device 20. Accordingly, a practitioner at a control device 20 can control and direct the adjustment of the slit height.

Figure 8C:
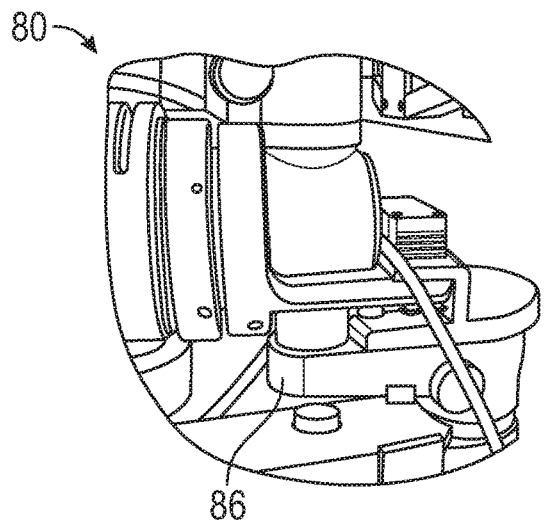
FIG. 8C is a perspective view of the slit angle adjustment member of the slit assembly of the ophthalmic device of FIG. 3.
Figure 8D:
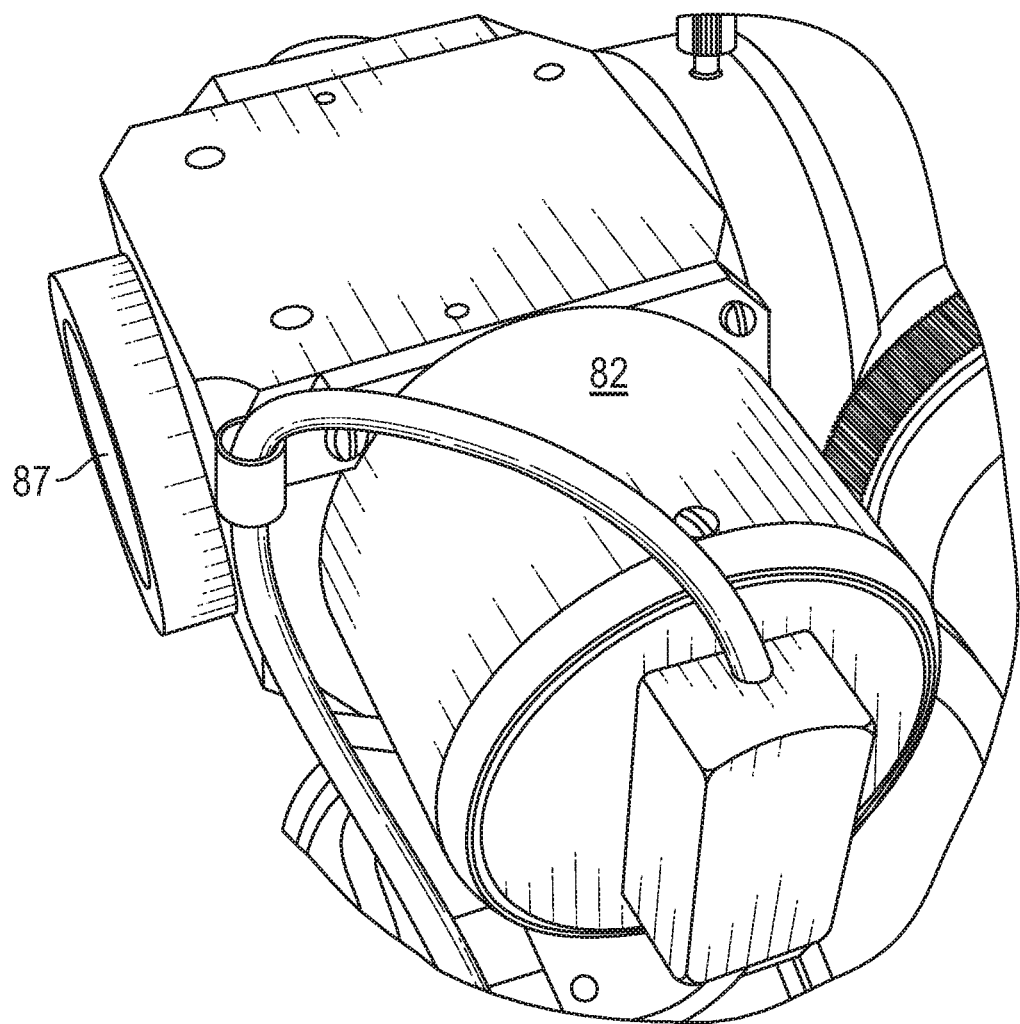
FIG. 8D is a perspective view of the magnification control of the slit assembly of the ophthalmic device of FIG. 3.

As shown in FIG. 8C, the slit assembly 80 of the present invention also preferably comprises a slit angle adjustment member 86 structured to adjust the angle of direction of the slit assembly 80. In at least one embodiment, the slit angle adjustment member 86 comprises a gear system coupled to a dedicated servo motor, such as model HS-7950™ (Hitec RCD USA Inc., Poway CA) having a three pole motor, dual ball bearing, and capable of generating a maximum torque of 343 ounce*inch, and is further disposed to physically adjust the angle of presentation of the slit. For example, a range of ±60° of rotation is required to adjust the slit angle. Accordingly, the gear assembly of the slit angle adjustment member 86 comprises an 54-teeth gear wheel attached to the servo which matingly engages the teeth of a 72-teeth gear wheel, thereby providing a gear ratio of 1:1.333. The 72-teeth gear wheel is fixed to the central column of the slit lamp assembly 80, and the servo is mounted atop the axis of rotation of the slit. Accordingly, movement of the servo rotates the servo gear wheel, in turn rotating the fixed gear wheel within ±60° of rotation, thereby driving the slit angle adjustment member 86 about the axis of rotation and correspondingly producing a differing angle of presentation of the slit in relation to the axis of rotation. Moreover, the dedicated servo for the slit angle adjustment member 86 is controlled by the processing assembly 60, such as a microcontroller, and is structured to respond to control messages from the control device 20. Accordingly, a practitioner at a control device 20 can control and direct the adjustment of the slit angle.

As mentioned previously and as shown in FIG. 8D, the slit assembly 80 may further comprise a slit lamp magnification control 82 structured to adjust the magnification of the ophthalmic device 10. For example, in at least one embodiment the slit lamp magnification control 82 comprises a detented magnification lens carrying turret that is structured to be adjusted by the rotation of a rotation member 87, such as a knob. The rotation member 87 is configured to rotate up to 360° in one direction. Accordingly, two servos each capable of rotating 180° are mechanically linked end to end, such as by an axle interface, to achieve 360° of rotation. For example, a first servo is fixedly secured to a mount and comprises an elongate axle disposed within the first servo and extending outwardly through the exterior of the servo. A second servo similarly comprises an elongate axle disposed therein and extending outwardly through the exterior of the second servo. However, the second servo is fixed to the rotation member 87. The first and second servos are disposed so that the axle of the first servo is in opposing and facing relation to the axle of the second servo, such as in an end-to-end fashion. Each axle is received in an axle interface, thereby mechanically linking the first and second servos. Since the second servo is secured to the rotation member 87, movement within the first servo is transferred to the second servo, which translates into rotation of the rotation member 87 and, correspondingly, adjustment of the magnification of the ophthalmic device 10 to achieve a higher or lower magnification. In at least one embodiment, the first and second servos are each model HS-5055MG (Hitec RCD USA Inc., Poway CA). In one embodiment, the magnification control 82 comprises a ruby lens positionable into and out of image capturing relation with the objective lenses 52', 52", in order to enable increased patient evaluation.

Accordingly, the various components of the slit assembly 80 can be adjusted and controlled from the control device 20 via control messages received and relayed by the processing assembly 60. The particular settings of the slit assembly 80 and its components permit maximized examination of the eye, as described above. Hence, the adjustment of various settings of the slit assembly 80, positioning assembly 70, and optic assembly 50 provide optimized image data.

The slit assembly 80 may further comprise a servo control system operable to utilize custom gearing to control a colored filter mechanism. The colored filter mechanism may include several colored filters, such as a blue filter and a yellow filter. The control device 20 can control the slit lamp light source 81 to produce different colored optical light beams. In an embodiment the slit lamp light source 81 can produce three colors, for example white, blue, and green (As shown in FIG. 10). These different colored light beams can be used in conjunction with vital dyes such as fluorescein or Rose Bengal to enhance imaging of corneal and conjunctival defects. The color filter mechanism may comprise of high efficiency dichroic filters to enhance Photodynamic Antimicrobial Therapy efficacy.

In still a further embodiment, the ophthalmic device 10 may comprise an electronic or digital caliper for acquiring measurements of portions of the patient's eye. Alternatively, control device 20 may comprise the electronic or digital caliper, which can be presented on the display 21 in conjunction with the images 24, 25. As shown on FIG. 10, a first button 231 is positioned proximate to the bottom left corner of the interface 23 and has a diagonal line to provide for unique visual reference. The first button 231 can be operable when selected by a practitioner to act as a digital caliper and can be an integrated point and click, two dimensional linear measurement system. The digital caliper can be calibrated to use the aspect ratio and area of the pixels from the images 24,25 to convert pixel measurements into physical measurements by scaling. This process can be repeated for each level of magnification. In other words, the two-dimensional linear measurement can be scaled to the image such that the measurement is associated with the dimensions of the patient's eye. For example, in FIG. 10, the measurement value is displayed in the "Distance" box in mm. An orientation angle of the measurement can be displayed in the "Angle" in degrees. For example, the angle measurement may refer to the angle created from the two dimensional linear measurement with respect to a vertical line.

These measurements can allow the practitioner to quantify anatomy and abnormalities in real-time with the data uploaded into a patient's electronic medical record. In another embodiment, measurements can be taken in three-dimensions by measuring the distance between planes of focus. These measurements could provide values of depth and curvature and could allow for the assessment of complex ocular structure and defects. This could be useful for angle closure glaucoma, cornea thickness, and anterior chamber depth.

Given the number of different control parameters that may be adjusted, in one embodiment the processing assembly 60 preferably comprises a setting memory structured to record the settings of the various components of the positioning assembly 70, optic assembly 50, and/or slit assembly 80 at a given configuration, and to return to these settings upon command. Accordingly, in such embodiment, the setting memory act as "shortcuts" that facilitate movement of the device to particular practitioners and/or patients and/or for certain desired views, and the control member(s) 22 comprise setting memory actuators structured to initiate movement of the ophthalmic device 10 into any of a plurality of preset settings. Furthermore, the setting memory can achieve certain intuitive control of the ophthalmic device 10 such as by predictively identifying or anticipating a progression of views or movements, suggesting adjustments and/or minimizing extraneous movements between positions.

Upon generation of the image data by the ophthalmic device 10, described above, the image data is sent to the control device 20 via a network 30, as discussed previously. It should be appreciated that other data, such as but not limited to audio data and patient information and feedback is also transmitted to the control device 20 via the network 30. The control device 20 therefore comprises transceiver capabilities operative to receive such data, including image and audio data, from the ophthalmic device 10 and to send control messages and audio from each practitioner(s) to the ophthalmic device 10. The data and images collected can be transferred to a patient's electronic medical record for treatment tracking and institutional record keeping. The electronic medical record can store the information related to the patient's eyes and its structures as well as the abnormalities and changes detected.

As shown in FIG. 9 and previously described, the display 21, which may include a single or multiple monitors, is structured to show image data 24, 25. The image data preferably comes from the first image capturing member 51' and the second image capturing member 51" and are displayed in adjacent non-overlapping relation to one another. These two images 24, 25 are of the same eye of the patient, obtained from slightly different angles by virtue of the different positions of the objective lenses 52' and 52", respectively. Hence, when a viewer 40 as described previously is implemented, a stereoscopic image is generated by the fusion of the first image data 24 with the second image data 25. Moreover, since the image data 24, 25 are each of high-definition resolution, the resulting stereoscopic image has an optimal degree of detail and clarity, thus permitting accurate and precise evaluation of the eye shown therein. As also shown in FIG. 9, the display 21 is further configured to present image data 26 from an external data capturing member 55, and therefore provide visual information to the practitioner(s) of the positioning of the patient in relation to the ophthalmic device 10. It should be appreciated that when multiple practitioners at different locations are using the present system 100, each practitioner is associated with a different control device 20 having its own display 21. Accordingly, practitioners can simultaneously view the same image data 24, 25, 26 on their respective displays 21.

In an embodiment wherein the display 21 is integrated with the control device 20, the control device 20 further comprises an interface 23 disposed on the display 21, as shown in FIGS. 9 and 10. The interface 23 comprises a visual representation of the current settings of the various components of the positioning assembly 70, slit assembly 80, and optic assembly 50 of the ophthalmic device 10. In at least one embodiment, such visual representation is a schematic representation, and if desired, the various adjustable aspects of the ophthalmic device 10, such as the slit width, slit height, slit angle, optical magnification, digital magnification, preset values of adjustment, and slit lamp intensity are presented as individual sliding scales or bars or selectable value, each having an indicator showing the current setting of the various aspects along their respective scales. For example, the slit width scale and indicator shows schematically the current setting for the slit width in relation to the range of possible settings for the width. The interface 23 also depicts information on the positioning of the ophthalmic device 10 as effected by the positioning assembly 70. In other embodiments, the settings of the various adjustable aspects of the ophthalmic device 10 are depicted diagrammatically or symbolically, such as by an odometer-type icon. Further, the position of the ophthalmic device 10, the nose and eyes of a patient, and the slit angle are represented symbolically, as depicted by the x-y box shown in FIG. 9, wherein the dot indicates the position of the ophthalmic device 10, the nose of the patient is represented as a triangle, the eyes of the patient are represented as the arrows, and the slit angle is indicated with an arc. In at least one embodiment, the interface 23 further comprises patient information, such as patient name, age, biographical information, medical history, medications, allergies, etc., and is supported by appropriate data entry software of the control device 20.

In FIG. 10, the control device 20 is operable to provide digital magnification of the captured image data via software. Where optical magnification can be capable of 40× magnification, digital magnification can be capable of 300× magnification. As shown on FIG. 10, a second button 232 is positioned above the first button 231 has a simplified image of a magnifying glass to provide for unique visual reference. The second button 232 can be operable when selected by a practitioner to provide digital magnification and can allow the practitioner to select a region of interest or a single point, activating the digital magnification algorithm in stepwise fashion by selecting on the screen. The digital magnification allows the displayed images 24, 25 to be magnified beyond optical magnification and for example, can facilitate the ability to take measurements with tools such as the digital caliper.

In FIG. 10, the interface 23 includes several indicators that including an optical magnification indicator ranging from at least 6× to 40× and operable to adjust the optical magnification, a light filter indicator operable to produce different colors including white, blue and green, a slit lamp height indicator ranging from 1 mm to 10 mm and operable to adjust the slit lamp height, a slit lamp light intensity indicator ranging from 10% to 100% and operable to adjust slit lamp light intensity, a slit lamp angle indicator ranging from −60 degrees to +60 degrees and operable to adjust slit lamp angle, a slit lamp width indicator ranging from 0.5 mm to 10 mm and operable to adjust lit lamp width, an "Eye" indicator with options of OS and OD referring to oculus sinister and oculus dextrus respectively and operable to switch image data 24, 25 between each eye of the patient, an "Unzoom" button operable to digitally unzoom and image enlargements with the magnification tool, a "Capture" button operable to capture the current images displayed, a zoom indicator operable to adjust and zoom in and out of the displayed image data 26, a z-axis indicator operable to move the ophthalmic device 10 along the z-axis and align the patient and image data 24, 25 into the desired orientation, and directional knobs that are operable to move the ophthalmic device 10 forwards, backwards, right or left, or in other words, along the x-axis and y-axis, to align the patient and the image data 24, 25, into the desired orientation.

Moreover, each of the indicators of the interface 23 are interactive, such that selecting and moving an indicator on the display 21 with a control member 22 results in the instantaneous creation of control message (s) that are transmitted in real-time over the network 30, where it is received by the processing assembly 60 of the ophthalmic device 10 and relayed to the appropriate component of the ophthalmic device 10 to dynamically adjust the settings of the various components, in substantially real-time to the generation of the control message(s). The interface can have control features that allow the practitioner to control the control members 22 with micro adjustments and preset stepwise intensities. Having dual control features can allow for switching between fine or coarse adjustments using the interface 23. Accordingly, the control members 22 have directing capabilities operative to control movements of the components of at least the positioning assembly 70, slit assembly 80, optic assembly 50, and processing assembly 60. By using the interface on either the primary or a supplemental display 21, an operator can effectively "jump" to desired or known parameters for a desired view rather than having to gradually manipulate to those parameters by sight.

For example, if a practitioner at the control device 20 uses a control member 22 (such as keyboard, computer mouse, and/or joystick) to slide the height indicator for the slit height to the right, corresponding control message(s) to increase the slit height is generated and transmitted by the control device 20. Upon receipt of the control message(s) the slit height adjustment member 85 will react and move to lengthen the slit height accordingly, in substantially real-time to the practitioner actuating the indicator on the interface 23 of the display 21. In such a manner, a practitioner can dynamically control and direct the adjustment of any movable component of the ophthalmic device 10 in real-time, even when separated by a great distance from the ophthalmic device 10. Further, when multiple practitioners are using the system 100 concurrently, any one of them can, at any time, interactively adjust or move any of the indicators of the interface 23 to send corresponding control messages from that particular control device 20 to the ophthalmic device 10, to interactively vary the settings of the components thereof. Such changes would then be reflected on the displays 21 of the other practitioners so that all practitioners can see any changes in the settings of the ophthalmic device 10 and corresponding changes in the image data 24, 25, 26 obtained thereby. Such changes, of course, would be realized in real-time as previously described.

The control device 20 may be operable to ameliorate user control latency by utilizing the interface 23 that includes an eye switching feature via a button press or quick selection feature. For example, FIG. 10 shows an option to select either OS or OD underneath the Eye indicator to switch between eyes. The eye switching feature allows the ophthalmic device 10 to position the optic assembly 50 to focus and place the selected eye in the center of display 21. This eye switching feature can allow the practitioner to switch from eye to eye with a button press and facilitates comparison between the two ocular surfaces.

In one embodiment, the interface 23 comprises duplicate and slightly different images structured to induce binocular disparity. Accordingly, the interface 23 controls may also be stereoscopic, and appear to "float" in front of the stereoscopic image of the eye of the patient. In a further embodiment, the interface 23 is positioned in unobscured view of the images 24, 25 of the patient eye, such as at a bottom edge or corner of the display 21. In one embodiment, the interface 23 is configured to fade away, become transparent or hidden, or otherwise not be visible when not in use.

Moreover, in at least one embodiment the display 21 is accessible, such as over the network 30, to a plurality of control devices 20 that can view the image data 24, 25, 26 and/or the interface 23, as well as control ophthalmic device 10. As noted, such an embodiment enables remote teaching and instruction to a group of people, as well as consultation with fellow practitioners, such as to seek advice, posit a question, and corroborate a diagnosis, for example. In such an embodiment, each of the plurality of displays can be disposed at different locations from one another, and may be remotely connected via the network 30, such as the Internet or world-wide-web, and all practitioners located in various different locations can simultaneously view image data from the ophthalmic device 10, verbally interact with the patient and each other, and take control of and operate the ophthalmic device 10 remotely.

In at least one embodiment of the present invention, the ophthalmic device 10 further comprises a clutch mechanism that is structured to increase the efficiency of the movement of the various components of the ophthalmic device 10, including the positioning assembly 70, slit assembly 80, optic assembly 50, and processing assembly 60. Specifically, the clutch mechanism is structured to actuate motion of a particular component of the ophthalmic device 10 from one position to a subsequent position only when the previous position is identified and returned to prior to moving to a subsequent position. By requiring that a throttle on a control member return to its previous position before moving to a new position, the clutch mechanism acts something like the neutral drive in a vehicle. This enables more precise control over the movements of the components of the ophthalmic device 10, creating smoother movements that are less susceptible to the large "jumps" currently common among devices controlling multiple actuators with a single controller. Specifically, the clutch mechanism comprises an electronic engagement mechanism to actuate motion only when the previous engagement position is selected. Normally, when controlling multiple actuators with a single mechanical interface such as a throttle interface, with only one axis of range of motion, a controlled actuator may be selected by the push of a button and switching between actuators will result in a large change in the commanded action of the newly selected actuator. The electronic clutch mechanism eliminates these jumps, and allows for more precise control of all actuators linked to the mechanical interface. This is accomplished by requiring the user to move the throttle back to its resting position, the position it was left in after its last command, before transmitting any new commands. Indicators on the interface 23 presented on the display 21 guide the user or practitioner to the engagement position to commence controlling. The benefits of such clutch mechanism are clear, since smoother motion of the parts of the ophthalmic device 10 and precise control of the same means less unintentional disturbance in transitions during an eye examination, and therefore, a more efficient examination. Accordingly, the clutch mechanism is responsive to control messages from the control device(s) 20, since control messages are relayed through the clutch mechanism to effect movement of the various components.

Further, in at least one embodiment of the system 100 for ophthalmic imaging, the ophthalmic device 10 is structured for remote activation such that the ophthalmic device 10 can be turned on from a command sent over the network 30 from any originating location. For instance, in one embodiment the processing assembly 60 of the ophthalmic device 10 comprises activation capabilities configured to respond to control message(s) generated by a control device 20 directing the device 10 to activate. In one embodiment, the activation capabilities comprise a motherboard configured to support the Ethernet networking standard Wake-on-LAN (WoL), although it should be appreciated that any structure and/or interface providing sufficient activating capabilities to enable remote activation of the ophthalmic device 10 is contemplated herein. Accordingly, a technician or attendant need not be present to turn the ophthalmic device 10 on for examination. A practitioner, system administrator, or other person can turn on the ophthalmic device 10 from any control device 20, or in some embodiments from any location accessible to the ophthalmic device 10 via a network 30, in order to, for example, provide updates and patches to the processing assembly 60, monitor and/or adjust the power management of the ophthalmic device 10, and prepare the ophthalmic device 10 for examination.

The system 100 for ophthalmic imaging can also be configured with the ophthalmic device 10 being structured for autonomous operation for select local data collection. Specifically, the ophthalmic device 10 can be structured to perform certain "pre-examination" procedures without instruction or control from a practitioner. Accordingly, the autonomous operation can occur even when there is reduced, limited, or no connectivity to the network 30 from which control messages can be received. In autonomous operation, the ophthalmic device 10 includes a series of audio commands that are transmitted through the audio member 78 to instruct the patient regarding the procedure, when and how to position their head on the patient positioning assembly 75, and distinct locations at which to look to facilitate obtaining image data of the various angles of the eye. For instance, the audio commands will direct the patient to look up, down, left, and right at designated times in order to obtain image data of the bottom, upper, right, and left sides of the eye, respectively.

Further, in the autonomous operation mode, the ophthalmic device 10 is structured and configured to record and save a plurality of video clips for later evaluation by the practitioner(s). These video clips coincide with the audio instructions, and comprise image data of the eye including, for example: direct illumination of the cornea and parts of the upper and lower eyelids, direct illumination of the upper eyelid, direct illumination of the lower eyelid, slit illumination focusing on the cornea at 45 degrees from the left side, slit illumination focusing on the lens at 45 degree from the left side, slit illumination focusing on the cornea at 45 degrees from the right side, and slit illumination focusing on the lens at 45 degrees from the right side. It should be appreciated that the above are merely examples of possible select local data collection, and are not intended to be limiting in any way. The ophthalmic device 10 is further configured to automatically focus on particular portions of the eye, such as the cornea, lens, and eyelids to acquire sharp image data. Further, the processing assembly 60 also comprises image pattern recognition capabilities to guide the movement of the various servos and motors of the ophthalmic device 10 along the x-, y-, and z-coordinates according to a preset program. This preset program and the series of audio commands cooperatively guide the patient and the ophthalmic device 10 through the autonomous operation mode. The autonomous operation mode can be operable to process the captured image data utilizing artificial intelligence powered by deep learning neural network algorithms, trained for identifying and diagnosing ocular injuries and disease.

Additional autonomous functions can be included in the control and operation of the ophthalmic device 10. The interface 23 can be operable such that the practitioner can select on screen a region that should be maintained in focus. Once the selected, the control device 20 can control the positioning assembly 70 to such that the servo motors reposition themselves to match the patient's eye movements to maintain in focus image data. The interface 23 can be operable to such that the ophthalmic device 10 remains centered with respect to a patients eye or centered with respect to a selected region by the practitioner. Similarly, the control device 20 can control the positioning assembly 70 to such that the servo motors reposition themselves to match the patient's eye movements to maintain centered image data.

Furthermore, the interface 23 can be operable to alternate between global focus of the eye or a region of interest and can be accomplished continuously, when initiated by the practitioner, or as a component during autonomous mode.

In at least one embodiment, the ophthalmic device 10 of the present system 100 can comprise a mounting stage structured to support the ophthalmic device 10 thereon and provide adjustment and positioning of the ophthalmic device 10 about multiple degrees of freedom. For example, the mounting stage is structured for secure rotation, tipping, tilting, and other movements, and may comprise a tri-axis goniometric cradle and rotation and tip-tilt stages. Accordingly, the mounting stage enables the ophthalmic device 10 of the system 100 to be used in examining a patient from a supine or reclined position. This can be particularly beneficial when the patient is unable to sit up and position himself/herself in the patient positioning assembly 75, such as an injured soldier on the battlefield or a patient in a hospital bed.

The ophthalmic device 10 can be structured such that its size and weight are compatible with standardized mounting stages and equipment for traditional ophthalmic instrument lane stands. For example, the ophthalmic device 10 is structured to be compatible with equipment and equipment accessories from National Vision.

The ophthalmic device 10 can be structured such that its sub components do not interfere with each other. Some of the components of the ophthalmic device 10 have a wide range of motion that are controlled using robotic hardware attached to cables for connectivity. These cables are positioned and structured such that they don't interfere with the optical path.

In some embodiments, the mounting stage also comprises at least one support member, which is structured to support the mounting stage from a floor, ground, or other surface. Moreover, the support member(s) are adjustable, such as telescopically, and may be independently adjustable of other support members to accommodate various terrains. As with the ophthalmic device 10, the mounting stage and its various components are responsive to and controllable by control messages sent from a control device 20 over a network 30.

In an embodiment the ophthalmic device 10 can be configured to operate with or without a table stand or mounting stage. In an embodiment the ophthalmic device 10 can be placed on the lap of a patient that is sitting upright. The processing assembly 60 may be disposed away from the remaining ophthalmic device 10 components, tethered only via cable or cables, and may allow for a reduced footprint of the ophthalmic device 10.

In an embodiment the processing assembly 60 and positioning assembly 70 are formed to be a retrofit kit and can be retrofitted to commercially available slit lamps. The retro fit kit can include the robotization components to be added to the commercially available slit lamp.

The present invention is further directed to a system for optimized stereoscopic viewing 200 at various distances, as depicted schematically in FIG. 11. Specifically, the system for optimized stereoscopic viewing 200 comprises a display 21 comprising at least one image, but preferably a pair of images, at least one viewer 40 comprising at least one prism 42 defining a prism angle and disposable a predetermined distance b, b' from the display, wherein the viewer 40 is operative for stereoscopic viewing of the image(s) and the prism angle is dependent on the predetermined distance b, b' between the viewer 40 and display 21 and/or the size of the image(s). In at least one embodiment, the display 21 comprises a first image 24 disposed in adjacent relation to a second image 25. In further embodiments, the first and second images 24, 25 are presented in non-overlapping fashion on the display 21. Accordingly, the system for optimized stereoscopic viewing 200 is structured to optimize side-by-side stereoscopy, and the viewer 40 is structured and operative to facilitate fusion of the first and second images 24, 25 into a single stereoscopic image at the predetermined distances b, b'.

The display 21 of the system for optimized stereoscopic viewing 200 is structured to present image data from any image source 210 capable of producing stereoscopic images. As used herein, an "image source" refers to the originating location of the image(s), such as the location of the physical object represented in the image data and/or the location where the image is generated. In at least one embodiment, the image source 210 comprises an ophthalmic device 10 as described above. However, the image source 210 is not limited to an ophthalmic device 10.

Moreover, the image source 210 is disposable in interconnecting relation with the display 21 and connects to the display 21 either directly or indirectly. Accordingly, in some embodiments, the system for optimized stereoscopic viewing 200 further comprises transmission capabilities operative to transmit at least one image from an image source 210 to a device having a display 21 over a network in substantially real-time relative to the generation of the image(s) at the image source 210, such as described above. Indeed, in one embodiment, the image source 210 is disposable in remote relation to the display 21, such that the image source 210 is located at a point distant from the display 21. "Remote relation" can refer to locations in different rooms, different buildings, different cities, and even different countries. In at least one embodiment, as in FIG. 11, the image source 210 comprises an ophthalmic device 10, and the display 21 of the system for optimized stereoscopic viewing 200 is structured to present image data 24, 25 from an ophthalmic device 10, as described above. However, in other embodiments the system for optimized stereoscopic viewing 200 comprises an image(s) not from an ophthalmic device 10, but from another image source 210. The system for optimized stereoscopic viewing 200 further comprises at least one viewer 40 as described previously. As illustrated in FIG. 11, the viewer 40 is disposable at a predetermined distance b, b' from the display 21. More specifically, the viewer 40 is disposable a first predetermined distance b from the display 21. For example, in at least one embodiment, the first predetermined distance b is defined as a short-range distance. In one embodiment, the first predetermined distance b is defined as in the range of about 50.8 centimeters to 88.9 centimeters. It should be appreciated that the limits of any range provided herein should not be interpreted strictly, and that distances falling slightly outside the range are still within the intended scope of the invention. As an example, a distance of 50.2 centimeters or 89.3 centimeters is within the intended scope of the invention for first predetermined distance b. In one embodiment, the first predetermined distance b is defined as in the range of about 55.9 centimeters to 76.2 centimeters. For instance, a comfortable viewing distance for a laptop computer is approximately 55.9 centimeters, and a comfortable viewing distance for a desktop computer is approximately 76.2 centimeters. Accordingly, in at least one embodiment, the first predetermined distance b is the typical distance in which a user sits in relation to a computer monitor, such as a desktop or laptop computer. In still other embodiments, the first predetermined distance b is defined as less than 50.8 centimeters, such as in the case of viewing a display 21 on a smartphone, tablet device, or other handheld computing device.

As shown in FIG. 11, the viewer 40 is also disposable at a second predetermined distance b' from the display 21, which is defined as a long-range distance. Moreover, the first predetermined distance b is less than, or shorter than, the second predetermined distance b'. For instance, in one embodiment, the second predetermined distance b' is defined as at least 88.9 centimeters. In another embodiment, the second predetermined distance b' is defined as at least 4.1 meters. Indeed, in one embodiment, the second predetermined distance b' is defined as in the range of about 0.4.1 meters to 13.9 meters, such as when the system for optimized stereoscopic viewing 200 is used in a large space, such as a classroom or auditorium, as depicted schematically in FIG. 12. In such embodiments, the display 21 comprises a screen, such as a projection screen, presentation board, or other similar surface having sufficient dimensions for presenting images of a large size for simultaneous viewing by multiple people and/or viewers 40. Accordingly, in the embodiment shown in FIG. 12, the second predetermined distance b' comprises any of a variety of distances from the display 21. Further, it is expected that different viewers used by practitioners at different locations will have different optimal prism parameters.

Figure 12:
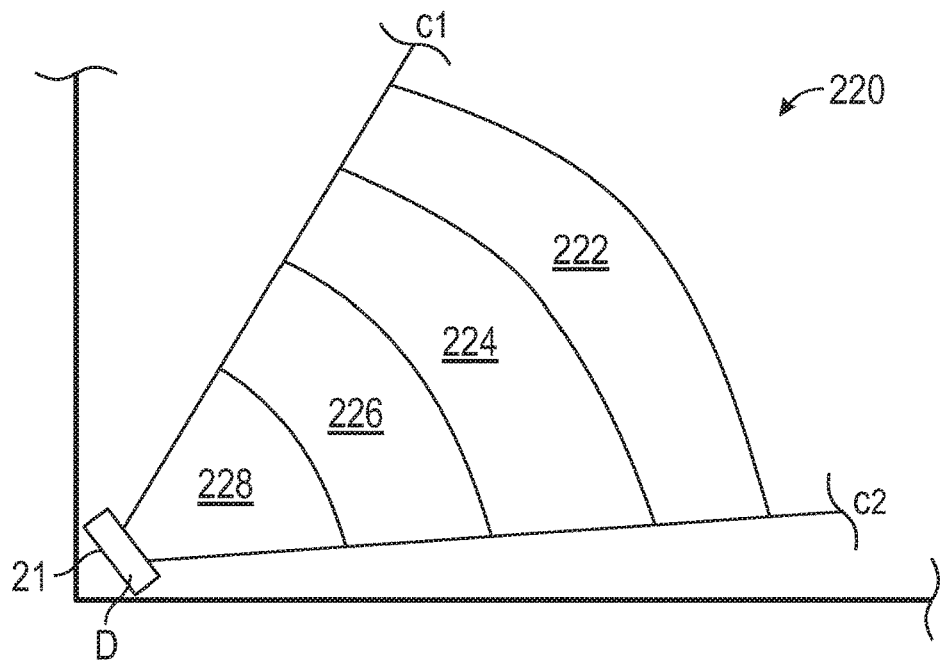
FIG. 12 is a schematic representation of the stereoscopic viewing of FIG. 11 optimized for distance viewing.

As shown by the dotted line in FIG. 11, the viewer 40 is disposable along a line of sight and at a predetermined distance b, b'. A "line of sight" is an imaginary line from the eye to a perceived object. As used herein, the "line of sight" refers to the visual path between the display 21 and image(s) 24, 25 presented thereon and the viewer 40 for stereoscopic viewing of the image(s) 24, 25. In some embodiments, as shown in FIG. 12, the line of sight is expanded to a viewing area 220 in which an observer implementing a viewer 40 can position himself/herself in order to view the stereoscopic image. As seen in FIG. 12, this stereoscopic viewing area is defined as the space between rays $C_1$ and $C_2$. Areas lying outside of the viewing area 220 do not permit or enable stereoscopic viewing of the image(s) 24, 25, even with a viewer 40.

Also, the image(s) 24, 25 comprise a size appropriate for the dimensions of the display 21 on which they are presented. For instance, in short range embodiments where the display 21 comprises a computer monitor, laptop monitor, or other computing device, the image(s) 24, 25 comprise a size in the range of about 12.7 centimeters to 81.3 centimeters. For example, on laptops the image(s) comprise a size of up to about 20.3 centimeters to 40.6 centimeters as limited by the actual lateral display size of the laptop display 21. On desktop computers, the image(s) comprises a size in the range of up to about 12.7 centimeters to 71.1 centimeters, depending on the actual lateral display size of the computer monitor as a display 21. In other embodiments, such as long-range applications where the display 21 comprises a screen or other large size, the image(s) 24, 25 comprise a size in the range of up to about 1.5 meters to 4.1 meters. It should be appreciated that the image(s) 24, 25 can comprise a smaller size than stated, such as when the display 21 comprises a plurality of images, so that the plurality of images can fit on the same display 21.

As previously noted and as shown in FIGS. 11 and 2A-2B, the viewer 40 preferably comprises at least one prism 42 structured to enable stereoscopic viewing of the image(s) 24, 25. As is commonly understood in the art, a prism is a transparent optical element having at least one side for deviating light at a particular angle, such as by refraction, reflection, polarization, or dispersion. The angle of deviation depends on a number of considerations, including the angle of incidence of incoming light (chief ray angle), the refractive index of the material through which the incident light travels to the prism, and the refractive index of the material comprising the prism. For example, the prism(s) 42 may comprise a material transparent to a particular desired wavelength of light. For instance, the prism(s) 42 may comprise a glass material, such as BK7, crown glass, fused silica (quartz), flint glass, heavy flint glass, plastics such as polymethylmethacrylate (PMMA), polystyrenes, polycarbonates, etc.

Moreover, the prism(s) 42 comprises any shape sufficient to bend and/or deviate the incident light in a predetermined desired manner. In this regard, in one embodiment such as shown in FIGS. 2A and 2B, each prism 42 comprises a triangular wedge shape having a triangular base and rectangular sides, and is disposed within the viewer 40 in order to direct the deviated light into the eyes of a person looking through the viewer 40.

For example, in FIGS. 2A and 2B the thicker dimension of the prisms 42 are disposed at the outer edges of the viewer 40, thereby deviating light inward toward the eyes of a person utilizing the viewer 40. In other embodiments, however, the prism(s) 42 comprises any shape necessary to deviate the incident light as desired and/or required.

Preferably disposed between the prisms is a partitioning element. This element helps to ensure that each eye sees a different image, thus optimizing the stereoscopic effect and minimizing the possibility of cross over effects.

Figure 13:
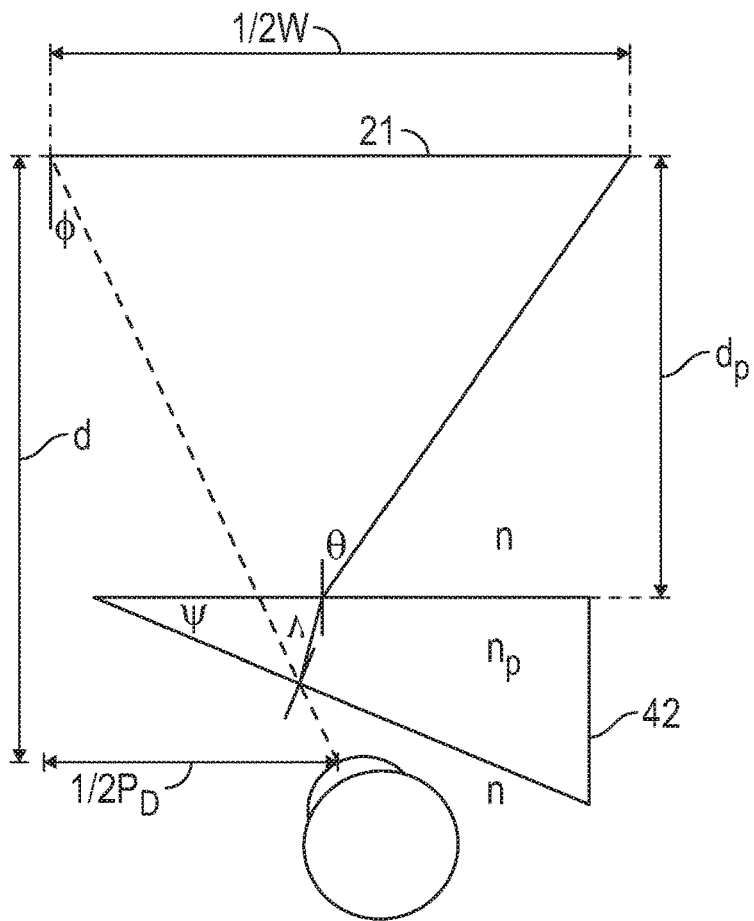
FIG. 13 is a schematic representation of the prism angle.

The prism(s) 42 of the viewer 40 define a prism angle. As shown in FIG. 13, the prism angle comprises the wedge angle of the prism (T) which intrinsic index of refraction of the prism's material ($n_p$) creates the angle of deviation of light produced by the prism ($\Phi$). The higher the index of refraction, the higher the angle of deviation of the light. Conversely, for a given angle of deviation, the higher the index of refraction, the lower the wedge angle has to be. This can be important to consider when reducing the bulk and weight of the prism. FIG. 13 shows a schematic depiction of a prism 42 in relation to an eye of an observer looking through a viewer, showing the relationship between the interpupillary distance ($P_D$), the distance from the eye to the object (d), the distance from the prism 42 to the object ($d_p$), the horizontal size or width of the object (w), the refractive index of the medium (n) and the prism ($n_p$), the prism angle ($\Psi$), the optical path length within the prism ($\Lambda$), and the chief ray angle ($\Theta$). Accordingly, Formula I below demonstrates the relationship between the chief ray angle, prism refractive index, interpupillary distance, the distance from the eye to the object, and the prism angle for optimized stereoscopic viewing at a number of different viewing distances:

$$n_p \sin\left[\Psi + \sin^{-1}\left[\frac{1}{n_p} - \sin(\Theta)\right]\right] = \sin\left[\Psi + \tan^{-1}\left[\frac{P_D}{2d_J}\right]\right]$$

Based on this formula, the prism angle $\Psi$ is dependent on at least one of the predetermined distance b, b', i.e. the distance from the eye to the object, represented as (d) in FIG. 13, and the size of the image, i.e. the width of the object, represented as (w) in FIG. 13. Therefore, based on Formula I and with reference to FIGS. 11 and 13, the prism angle is proportional to the size of the image(s) 24, 25 in that a larger prism angle $\Psi$ is required for larger sized image(s) 24, 25. Similarly, the prism angle $\Psi$ is inversely proportional to the predetermined distance b, b' (also shown as (d) in FIG. 13) between the viewer 40 and the display 21. That is to say, a larger prism angle $\Psi$ is required when the predetermined distance b, b' is smaller, such as when the observer is closer to the display 21.

As one example for illustrative purposes, in at least one embodiment of the system for optimized stereoscopic viewing 200, the prism is made of plastic (PMMA), which has a prism angle $\Psi$ in the range of about 9° to 30° and an index of refraction of 1.49. As before, this range is not meant to be strictly interpreted, and in fact slight variations above and below the outer limits are contemplated. For instance, a prism angle $\Psi$ of 8.7° or 30.3° are still within the spirit and scope of the present invention. Moreover, in at least one embodiment the prism angle $\Psi$ is chosen from the group consisting of generally about 10°, 16°, 20°, 25°, and 30°. It should be noted that these stated prism angles y are approximations, such that slight variations therefrom are contemplated. For example, a prism angle $\Psi$ of 10.2° or 24.7° are within the spirit and scope of the present system 200. Of course, for prisms 42 made of different materials with different indices of refraction, different ranges of prism angles $\Psi$ will apply.

Further, at certain predetermined distances b, b', a particular prism angle $\Psi$ will be most appropriate, such as based on Formula I, although other prism angles y may be used effectively at the same predetermined distances b, b', albeit with less optimal depth impression. For example, in long-range embodiments such as shown in FIG. 12, a viewer 40 having prisms 42 with prism angles $\Psi$ in the range of 9.2° to 10.8°, but preferably 10°, will enable optimal stereoscopic viewing at predetermined distances falling in a first viewing area 222, which is defined as between approximately 10 meters and 14 meters from the display 21, although in some embodiments this limit may extend beyond 14 meters. However, and for example, a viewer 40 having a prism angle $\Psi$ of 16° may also be used in parts of the first viewing area 222 and will produce a fused image, but the stereoimage produced will not have as much depth detail as other prism angles $\Psi$ could produce in that viewing area. Accordingly, there is an overlap of prism angles $\Psi$ possible for each viewing area. Similarly, a viewer 40 having prisms 42 with prism angles $\Psi$ in the range of 13.6° to 18.4°, but preferably 16°, will optimally enable stereoscopic viewing at predetermined distances falling in second viewing area 224, which is defined as between approximately 8 meters and 10 meters from the display 21. Also, a viewer 40 having prisms 42 with prism angles $\Psi$ of 25° will optimally enable stereoscopic viewing at predetermined distances falling in third viewing area 226, which is defined as between approximately 4 meters and 8 meters from the display 21". However, stereoscopic viewing is not enabled for area 228, which is defined as distances falling between the display 21 and approximately 4 meters therefrom.

Further, the same viewer 40 having prisms 42 can be used for shorter predetermined distances b as well as longer predetermined distances b'. For example, a viewer 40 having a prism angle $\Psi$ of approximately 16° can be used for viewing images 24, 25 on a desktop computer having a 19 inch advertised size monitor as a display 21, as well as in a larger room at a distance of between $b_2$' and $b_3$' wherein the images 24, 25 are presented on a presentation screen as a display 21. As another example, viewing stereoimages located a short predetermined distance, such as in the range of about 50.8 centimeters to 88.9 centimeters, can be accomplished with viewers having a prism angle in the range of about 9° to 29°. For distances in the range of about 55.9 centimeters to 76.2 centimeters, viewers having a prism angle in the range of about 18° to 22° can be used. And generally for distances in the range of up to about 12.7 centimeters to 81.3 centimeters, viewers having a prism angle in the range of about 9° to 29° can be used. Finally, for distances in the range of 1.5 meters to 2 meters, viewers having a prism angle of about 9.2° to 10.8° are preferred.

Figure 14:
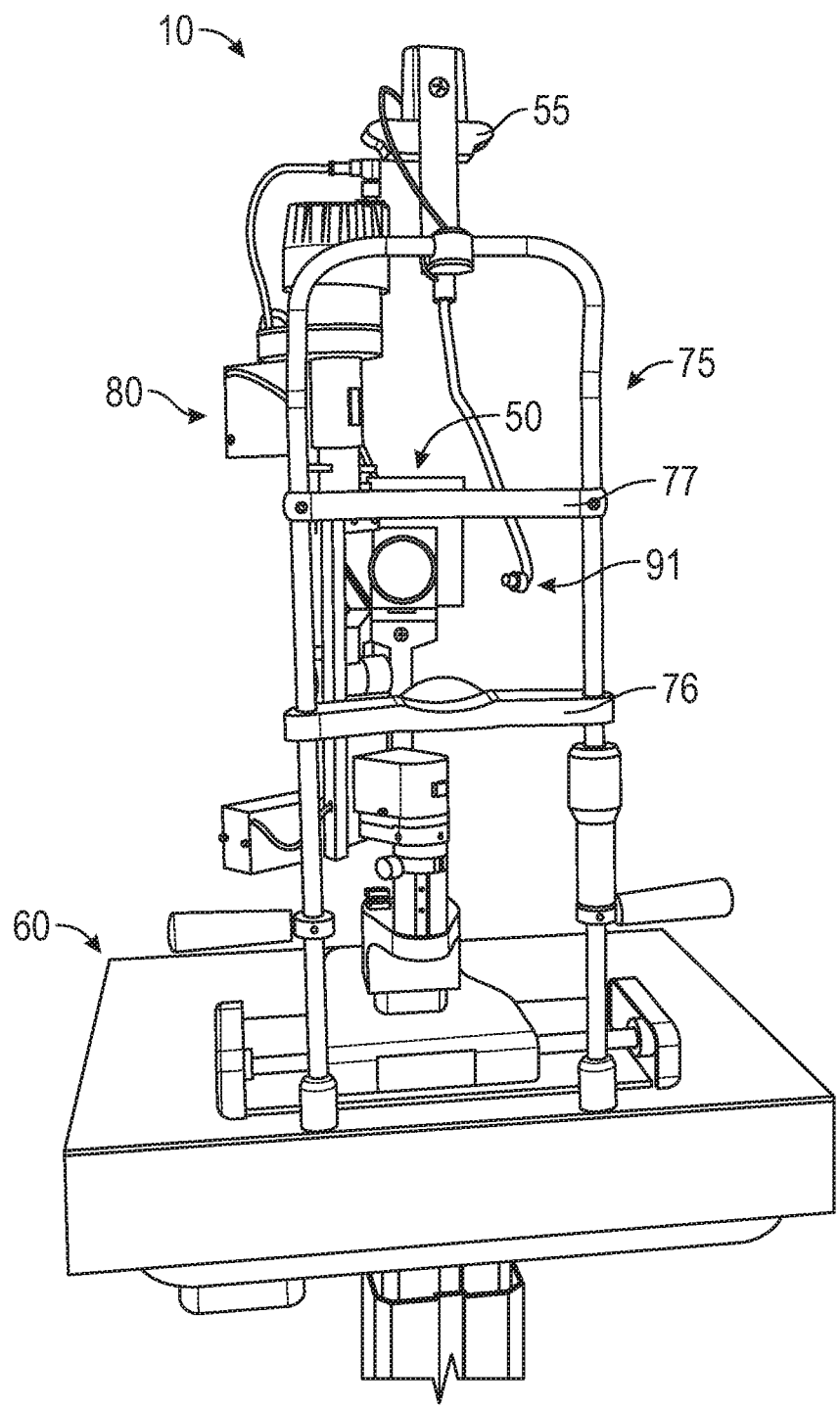
FIG. 14 is an example embodiment of an ophthalmic device shown in FIG. 4.

FIG. 14 is an example embodiment of an ophthalmic device. In an embodiment the ophthalmic device includes a device 91. In an example, the device 91 can be a motorized cornea sensitivity assessment tool that is operable to activate a pulsed fluid jet to assess and quantify nerve function at various locations on the cornea and limbus. This could be useful in assessing corneal nerve function in cases of traumatic injuries (chemical burns, dry eye). Alternatively the device 91 can be a motorized treatment delivery device or a motorized gaze fixation device.

The control device 20 can provide numerical control and direct changes in the positioning and parameters of the various components of the ophthalmic device 10 with open and closed looped systems where image feedback data is provided to the controller to improve and correct for errors in positioning. The processing system 60 can perform precise measurements along the three axes, X, Y, and Z which are orthogonal to each other in a three-dimensional Cartesian coordinate system.

In an embodiment the ophthalmic device 10 includes an integrated light source suitable for illuminating an examination room and the patient with diffused indirect light. The integrated light source permits the practitioner to have additional control (intensity and directionality) of ambient lighting.

In an embodiment the ophthalmic device 10 can include a photosensitivity module that can quantify the patient's visual photosensitivity discomfort threshold before initiating the exam of the patient. Photosensitivity varies among patients, and thus a practitioner must balance between the patient's comfort and the need to properly examine the eye. The ophthalmic device 10 can factor in this threshold to recommend a suitable light intensity to the practitioner. In addition, during the exam, the ophthalmic device 10 can warn the practitioner when the threshold has been exceeded.

In an embodiment the ophthalmic device 10 can be integrated with a screen or display 326 that is operable to display video and audio in real-time with the practitioner. The display 326 can allow the patient to communicate with the practitioner and help narrow the personal and professional gap in the patient doctor relationship. For example, before and after the examination, the patient can interact with the practitioner, allowing a supportive interchange to foster.

In an embodiment the ophthalmic device 10 can include a sensor that measures temperature and humidity of the location of the ophthalmic device 10 and patient. The temperature and humidity can be displayed on the display 21 in real-time and can be saved to the electronic record.

In an embodiment the ophthalmic device 10 can include a specialized accessory port. The specialized accessory port can be outfitted with a photodynamic therapy unit, and be operable for treating infections of the cornea. The photodynamic therapy unit can be remotely operated. The photodynamic therapy unit can be operable to produce a light beam and control the wavelength and intensity of the produced light beam, depending on the photosensitizer utilized for the treatment. The photodynamic therapy unit can include an integrated protocol timer and intensity calculator, which can allow the practitioner to customize the treatment duration and intensity depending on the level of treatment required.

In an embodiment the ophthalmic device 10 can include a robotized optical accessory such as a Hruby lens to image the posterior segment of the eye. Similar to other components, the practitioner can control the spatial orientation of the robotized optical accessory via the display with on-screen user controls such as the interface 23.

In an embodiment the ophthalmic device 10 can include an accessory operable to measure or quantify the pressure in an eye globe. The accessory may comprise a motorized puff tonometer. The accessory can be robotized and operated via software incorporated in the control device 20. The measured pressure data can then be synchronized to the patient's electronic medical record for treatment tracking and institutional archiving.

The ophthalmic device 10 can utilized image capturing members 5, processing assembly 60, and positioning assembly along with the control device to measure and produce a topographical map of the corneal surface of a patient via a quantitative photogrammetric method that produces measurements and indices that describe the corneal shape, such as symmetrical, regularly astigmatic, and keratoconic, as well as the scleral sharp. The topographical map can be used to map the tridimensional surface and volume of abnormal growths and dips as they occur in cases of abnormal tissue growth, malignancies and infections on the ocular and iris surfaces. The precise tridimensional measurements of these surfaces could allow for quantitative measurements of treatment efficacy. This can be directed at cases of infectious corneal melts, keratoscleritis, conjunctival necrosis, basal and squamous cell carcinoma, lymphoma, sebaceous carcinoma, primary acquired melanosis, Steven-Johnson syndrome as well as iris melanoma, cysts.

In an embodiment the control device 20 can be operable to provide superposition of images and graphics of the eye and other pertinent information derived from complementary examinations at controllable levels of transparency over the live patient image that can be shown on the display 21. For example, the superposition overlays may include corneal topography, tear film, OCT cross sections and en face projections, biometry measurements, and slit lamp photographs from previous imaging session. Furthermore, Fundus photographs and OCT images of the retina may also be appropriate. The superposition images or layers can be aligned with rigid body and affine transformations, locked to the current live image and follow the live image during examination.

In an example the ophthalmic device 10 can include a laser system for photocoagulation treatment including blocking bleeding vessels. In an example the ophthalmic device 10 can include a laser system for photo disruption to, for example, cut unwanted intraocular membranes including an opacified posterior lens capsule that can occur months or years after cataract surgery with intraocular lens implantation.

Reference throughout this specification to "one embodiment" or "an embodiment" means that a particular feature, structure, or characteristic described in connection with the embodiment is included in at least one embodiment. Thus, appearances of the phrases "in one embodiment" or "in an embodiment" in various places throughout this specification are not necessarily all referring to the same embodiment. Furthermore, the particular features, structures, aspects, or characteristics of the various embodiments and examples may be combined.

Since many modifications, variations and changes in detail can be made to the described preferred embodiment of the invention, it is intended that all matters in the foregoing description and shown in the accompanying drawings be interpreted as illustrative and not in a limiting sense. Thus, the scope of the invention should be determined by the appended claims and their legal equivalents.

What is claimed is:

1. An ophthalmic device for obtaining stereoscopic images of at least one eye of a patient, the ophthalmic device comprising:
   a slit assembly including:
      a light source;
      a slit width adjustment member;
      a slit height adjustment member; and
      a slit angle adjustment member;
   an optic assembly including at least two image capturing members disposed within the patient's optical pathway to capture image data of at least one eye of a patient;
   a positioning assembly including:
      a first positioning member coupled to the slit assembly and the optic assembly; and
      a second positioning member coupled to the slit assembly and the optic assembly; and
   a processing assembly in electrical communication with the slit assembly, optic assembly, and positioning assembly, the processing assembly configured to receive image data from the optic assembly, and the processing assembly operable to transmit the image data;
   wherein the optic assembly does not include a beam splitter.

2. The ophthalmic device of claim 1, wherein the at least two image capturing members are high resolution cameras.

3. The ophthalmic device of claim 1, wherein the ophthalmic device further includes a Hruby lens.

4. The ophthalmic device of claim 1, wherein the optic assembly further includes an ambient light source.

5. The ophthalmic device of claim 1, wherein the ophthalmic device further includes a display operable to display video and audio to the patient.

6. The ophthalmic device of claim 1, wherein the ophthalmic device further includes a photodynamic therapy unit operable to treat infections.

* * * * *